US010638679B2

(12) United States Patent
Rademacher

(10) Patent No.: US 10,638,679 B2
(45) Date of Patent: May 5, 2020

(54) METHOD FOR THE GENERATION AND CULTIVATION OF A PLANT CELL PACK

(71) Applicant: FRAUNHOFER-GESELLSCHAFT ZUR FÖRDERUNG DER ANGEWANDTEN FORSCHUNG E.V., München (DE)

(72) Inventor: Thomas Rademacher, Aachen (DE)

(73) Assignee: Fraunhofer-Gesellschaft zur Förderung der angewandten Forschung e.V, München (DE)

( * ) Notice: Subject to any disclaimer, the term of this patent is extended or adjusted under 35 U.S.C. 154(b) by 884 days.

(21) Appl. No.: 14/370,109

(22) PCT Filed: Jan. 31, 2013

(86) PCT No.: PCT/EP2013/000296
§ 371 (c)(1),
(2) Date: Jul. 1, 2014

(87) PCT Pub. No.: WO2013/113504
PCT Pub. Date: Aug. 8, 2013

(65) Prior Publication Data
US 2014/0342455 A1        Nov. 20, 2014

Related U.S. Application Data

(60) Provisional application No. 61/592,780, filed on Jan. 31, 2012.

(30) Foreign Application Priority Data

Jan. 31, 2012  (EP) ..................................... 12000618

(51) Int. Cl.
  *A01H 4/00*       (2006.01)
  *C12N 15/82*      (2006.01)

(52) U.S. Cl.
  CPC ........... *A01H 4/00* (2013.01); *C12N 15/8257* (2013.01)

(58) Field of Classification Search
  None
  See application file for complete search history.

(56) References Cited

U.S. PATENT DOCUMENTS

| 6,740,526 B1    | 5/2004 | Curtis |
| 2002/0092037 A1 | 7/2002 | Connett-Porceddu et al. |
| 2009/0165175 A1* | 6/2009 | Ji .......................... A01H 4/005 800/294 |

FOREIGN PATENT DOCUMENTS

| WO | 200510327 A1 | 11/2005 |

OTHER PUBLICATIONS

Freshney (Basic Principles of Cell Culture. Culture of Cells for Tissue Engineering, edited by Gordana Vunjak-Novakovic and R. Ian Freshney, Charpter 1, 3-23, 2006).*
Mustafa et al (Initiation, growth and cryopreservation of plant cell suspension cultures. nature protocols vol. 6, 715-742, published online May 2011).*
Wilson et al (Recent advances towards development and commercialization of plant cell culture processes for the synthesis of biomolecules. Plant Biotechnol J. 10:249-268, 2012, published online Nov. 8, 2011).*
Srivastava et al (Hairy Root Culture for Mass-Production of High-Value Secondary Metabolites. Critical Reviews in Biotechnology, 27:29-43, 2007).*
Hellwig et al (Plant cell cultures for the production of recombinant proteins. Nature Biotechnology vol. 22, 1415-1422, 2004).*
Mustafa et al (Initiation, growth and cryopreservation of plant cell suspension cultures, nature protocols vol. 6, 715-742, published online May 2011). (Year: 2011).*
Srivastava et al (Hairy Root Culture for Mass-Production of High-Value Secondary Metabolites. Critical Reviews in Biotechnology, 27:29-43, 2007). (Year: 2007).*
Wilson et al (Recent advances towards development and commercialization of plant cell culture processes for the synthesis of biomolecules. Plant Biotechnol J. 10:249-268, 2012, published online Nov. 8, 2011). (Year: 2011).*
Hellwig et al (Plant cell cultures for the production of recombinant proteins. Nature Biotechnology vol. 22, 1415-1422, 2004). (Year: 2004).*
FraunhoferInstitute for Molecular Biology (plant cell pack protocol , 2016) (Year: 2016).*
Sangwan R.S. et al. "Direct Fluorometry of phase-extracted tryptamine-based fast quantitative assay of l-tryptophan decarboxylase from Catharanthus roseus leaf." Anal Biochem 1998, 255:39-46.

(Continued)

*Primary Examiner* — Medina A Ibrahim
*Assistant Examiner* — Wayne Zhong
(74) *Attorney, Agent, or Firm* — Saffire IP; Daren P. Nicholson

(57) ABSTRACT

The present invention relates to the generation and cultivation of plant cell material in the form of a non-tissue multilayer cell pack and its use for the accumulation or harvesting of a desired product. In particular, the invention provides a method for the generation of plant cell material in the form of a medium-deprived, porous structured and non-tissue multilayer cell pack and for the subsequent maintenance of said cell pack, comprising the steps of (i) providing a cell pack by separating cells from a plant cell suspension culture, wherein the content of the liquid comprised by the cell pack is reduced and adjusted to correspond to a cell pack density between 0.1 and 0.9 g wet cell weight per cm3, thereby establishing the medium-deprived and porous structured nature of said cell pack, and (ii) incubating said medium-deprived and porous structured cell pack in a non-liquid environment under a relative humidity of 50 to 100%.

20 Claims, 13 Drawing Sheets

(56) References Cited

OTHER PUBLICATIONS

Di Fiore S. et al. "Targeting tryptophan decarboxylase to selected subcellular compartments of tobacco plants affects enzyme stability and in vivo function and leads to a lesion-mimic phenotype." Plant Physiol , 2002, 129:1160-1169.
Helens R. et al. "A Guide to Agrobacterium Binary Ti Vectors." TIBS, 2000, 5:446-451.
Hellwig S. et al. "Plant cell cultures for the production of recombinant proteins." Nature Biotechnology, Nov. 1, 2004, 22(11):1415-1422, XP002420852, Nature Publishing Group, NY, NY, ISSN: 1087-0156.
Holland T. et al. "OPtimal ritrogen supply as a key to increased and sustained production of a monoclonal full-size antibody in BY-2 suspension culture." Biotechnol Bioeng 2010, 107:278-289.
Lindbo J.A. "TRBO: a high-efficiency tobaco mosaic virus RNA-based overexpression vector." Plant Phys 2007, 145:1232-1240.

\* cited by examiner (A)

(B)

(A)

(B)

(C)

(D)

(A)

(B)

(C)

(A)  (B)  (C)

(A)

(B)

METHOD FOR THE GENERATION AND CULTIVATION OF A PLANT CELL PACK

CROSS REFERENCE TO RELATED APPLICATIONS

This is a national phase application under 35 USC § 371 of international patent application serial no. PCT/EP2013/000296 filed 31 Jan. 2013, which claims priority to European patent application no. EP 12 000 618.4 filed 31 Jan. 2012 and U.S. provisional patent application no. U.S. 61/592,780; the contents of each are herein incorporated by reference in their entirety.

TECHNICAL FIELD

The present invention relates to the field of plant biotechnology. In particular, the present invention relates to the generation and cultivation of plant cell material in the form of a non-tissue multilayer cell pack and its use for the accumulation or harvesting of a desired product.

BACKGROUND OF THE INVENTION

During the past decades, enormous efforts have been dedicated to the establishment and culturing of plant-based systems for the accumulation and harvesting of native or heterologous proteins and secondary metabolites. The literature provides a vast quantity of evidential material that proves the utility of plant-based systems to produce a large variety of desired substances that are either secreted into the culture medium or isolated from the producing cells, tissues, organelles or even whole plants or parts thereof. Likewise, a broad range of transformation protocols exist that ensure the establishment of either stably or transiently transformed plant material. However, there is still a need for a reliable, relatively cost-efficient and rapid technology to obtain high yields of a desired product from plant cells.

SUMMARY OF THE INVENTION

The present invention is thus concerned with the provision of a plant-based system to produce high levels of desired native or recombinant products that makes use of cells from a plant cell suspension culture and overcomes the problems of the prior art, in particular with respect to the necessity of handling large volumes of culture medium during cultivation and subsequent processing, including product removal, extraction and purification.

Accordingly, the present invention is concerned with the expression or generation of native or recombinant proteins and metabolites and uses specific plant cell material derived from commonly established plant cell suspension cultures as a production host.

Contrary to many currently used and developed systems that are based on the use of intact plants or at least intact and differentiated plant tissue, the use of suspension cells has the advantage that homogeneous material can be reproducibly produced under controlled, aseptic and contained conditions.

There are currently two principal strategies to express recombinant proteins in plants, namely (i) the generation of stable transgenic plants or suspension cell lines or (ii) the transient expression of heterologous gene(s) after infecting the plant expression hosts (plant, tissue or cells) with a bacteria (e.g. *Agrobacterium*), a virus (e.g. Tobacco Mosaic Virus, Potato virus X/Y, Cowpea mosaic virus and many others), or a combination of both (e.g. magnifection) to enable the host to express the heterologous genetic information (DNA or RNA).

Although the invention also comprises the use of stably transformed plant cell material, systems for the transient expression have the advantage of speed (gene-to-product, time-to-market, emergency response) as well as the possibility to achieve accumulation levels that are much higher than those that can typically be obtained in stably transformed transgenic plants or parts thereof such as cells.

According to a preferred embodiment, the present invention thus combines the advantages inherent to plant suspension cultures with the advantages of the transient expression systems.

The addition of Agrobacteria to a plant suspension culture followed by further cultivation of the plant cells and the bacteria in suspension has already been tried and published (see U.S. Pat. No. 6,740,526 B1) but the described approaches suffer from low transformation efficiency. Moreover, the Agrobacteria quickly overgrow the plant suspension cells unless effective measures like use of antibiotics to kill the bacteria or use of auxotrophic strains to suppress growth are taken. Others have described direct detrimental effects (cell death, hypersensitive response) of the co-cultivated bacteria on the plant suspension cells. As a consequence, there currently does not exist a plant-based production system that combines the efficiency of transient Agroinfiltration/viral infection of intact plants or tissues with the advantages of plant suspension cultures and enables production of homogeneous biomass, preferably under aseptic controlled conditions which is of tremendous advantage for establishing a GMP compliant production. As mentioned above, the approach of co-fermentation as disclosed in U.S. Pat. No. 6,740,526 B1 suffers from low transformation efficiency and concomitant bacterial over-growth, whereas leaf-based systems realize high transformation efficiency but, however, encounter problems with up-scaling, suffer from low space-time yields for initial biomass production and rely on controlled but not aseptic conditions for plant biomass production. The high production costs as compared to microbial systems are the main reason why these systems have not gained widespread interest and use as production systems for biologicals. As a consequence, research and development targets more specialized applications where the combined advantage of speed and production robustness are important, i.e. emergency response (e.g. Flu vaccines, new-emerging diseases, personalized medicine etc.). These problems as well as the provision of improved means for manipulating the genetic background of any given plant host material are addressed and solved by the invention.

According to the invention, there is provided a method for the generation of plant cell material in the form of a medium-deprived, porous structured and non-tissue multilayer cell pack and for the subsequent maintenance of said cell pack, comprising the steps of (i) providing a cell pack having a porous structure by separating cells from a plant cell suspension culture, wherein the content of the liquid comprised by the cell pack is reduced and adjusted to correspond to a cell pack density between 0.1 and 0.9, preferably between 0.2 and 0.85, most preferably between 0.4 and 0.8 g wet cell weight per $cm^3$, thereby establishing the medium-deprived and porous structured nature of said cell pack, and (ii) incubating or cultivating said medium-deprived and porous structured cell pack in a non-liquid environment under conditions maintaining or restoring the porous structure of said cell pack while providing sufficient humidity, i.e. a relative humidity of 50 to 100%, in order to prevent the plant material from severe desiccation.

As will be acknowledged by a skilled person, cells within a tissue typically have intimate connections, are usually differentiated and frequently exhibit particular morphologies and polarized cells. Moreover, cells within a tissue usually have characteristic orientations relative to each other.

In contrast, the cell packs according to the invention are generated from plant cell suspension cultures. A particular property of the plant cell suspension cultures is that individual cells or aggregates of several cells are moving or moveable relative to each other and do not exhibit a higher organizational level.

As a consequence, cell packs according to the invention comprise individual cells and cell clusters that have no particular relative orientation to each other. These cells are casted in such a way that the resulting conglomerate packs into a three-dimensional porous structure that has significant air voids. There is a clear correlation between the density of the cell pack and the presence of the air voids. The air voids are important for several reasons. First, they enable efficient gas exchange such that sufficient amounts of oxygen can be easily supplied to the cells. Second, the air voids can temporarily and easily be flooded again with liquids (=treatments). Such temporary treatments can be used to bring various agents into close contact with all cells of the cell pack, thereby providing an efficient method for genetic transformation, biotransformation, product recovery through elution or washing of the cell pack, application of substrates or analytes for diagnostic purposes (e.g. cell pack based immunoassays). It is important that these treatments are only temporary and that the porous structure of the cell pack is reconstituted and the density of the cell pack is confirmed to ensure high viability during the subsequent incubation steps. Due to the porous nature of the cell pack it is furthermore important in certain applications that the humidity is sufficiently high to prevent the cell pack from drying out because of the high surface area that is in contact with the gas phase at the cell/air void interface.

In particular, a preferred embodiment of the method according to the invention comprises (i) a first cultivation step in which a plant cell suspension is cultured, preferably under controlled and/or aseptic conditions, for the provision of a homogeneous plant biomass, (ii) a separation step in which the liquid media is separated from the plant cells in such a way that a porous cell pack with a density between 0.1 and 0.9, preferably between 0.2 and 0.85, most preferably between 0.4 and 0.8 g wet cell weight per $cm^3$ is generated, and (iii) a second cultivation step in which the cell pack is further incubated in a non-liquid environment under controlled conditions (see above) for at least another day. Depending on the actual situation and the practitioner's intent, this second cultivation step may be performed for several days. Typically the second cultivation step is performed for 2 to 7, preferably for 3 to 5 days.

In all current state-of-the-art cultivation methods the plant cell material is in direct or indirect (porous support or membrane-mediated) contact with a nutrient containing medium continuously, i.e. most of the times. The continuous medium contact is only interrupted briefly (i.e. short time periods) when cells are transferred from one medium to another. Cells may be filtered or washed to remove "old" medium but are then quickly transferred into a new medium.

In contrast to prior art this cultivation step is conducted under conditions which maintain the viability of the cells and promote product accumulation with reduced or minimal cell growth and division. This was achieved by cultivating well aerated packed cells in a moist environment, preferably without contact to a liquid or gelled growth medium from which components or nutrients diffuse into the cell pack (US2002/092037 A1; WO2005/103271 A1). In prior art thin layers of cells are plated or spotted on supportive membranes placed on medium in order to supply nutrients to the cells. However, cultivation of cell layers on growth medium has the disadvantage that only small amounts of biomass can be treated due to the need of contact to the medium. In contrast, the cell pack method of the invention is independent of a supporting medium, is scalable and thus suitable for industrial applications. Accordingly, the above incubation or cultivation step (ii) is carried out in a non-liquid environment, preferably without placing the medium-deprived and porous structured cell pack on or in any contact to a (liquid or gel-solidified) maintenance or growth medium.

According to a preferred embodiment of the method according to the invention the second cultivation step is performed for weeks or month. In such cases the cultivation conditions may have to be modified to maintain the viability of the cells. This can for example be achieved by temporarily (i.e. for a time period up to 3 hours, preferably up to 1 hour) providing nutrients to the cell pack and/or by reducing the incubation temperature.

In the prior art, a suspension culture is used to accumulate a desired product which remains within the cells comprised by the culture or is secreted into the culture medium. When the production period is over, the cells are either destroyed in order to harvest the accumulated product or discarded. Stably transformed plant cells in suspension, i.e. immersed in liquid media, have been used to produce a broad spectrum of different therapeutic recombinant proteins (S. Hellwig et al., "Plant cell cultures for the production of recombinant proteins", *Nature Biotechnol* 22: 1415-1422, 2004).

According to the invention, the cells comprised by the suspension culture are used to generate a medium-deprived non-tissue plant cell material in a form of a porous structured cell pack further defined by having a specific density as mentioned above. This cell pack which optionally may be provided in a user-defined shape can be regarded as an artificially generated multilayer cell conglomerate or cell cake consisting of undifferentiated plant cells that have been grown in liquid culture. The source cells can be stably and/or transiently transformed transgenic cells, mutated cells or wild-type (native) cells able to accumulate a desired product. By casting the cell suspension into the structure of a cell pack while removing most of the surrounding liquid medium, a three-dimensional porous plant cell material is generated. Although filtering techniques such as vacuum filtration, pressure filtration and centrifugation through a filter is preferred, the liquid medium can also be removed by other means (e.g. separators used in food industry, continuous centrifugation) known in the art as long as the above cell pack density is ensured. The establishment, maintenance and/or re-establishment of air voids between individual cells or cell clusters comprised by the cell pack provides a porous structure of the cell pack assuring good aeration (gas exchange), which is a crucial factor for the viability and the productivity of the packed plant cell material during the second cultivation phase. In the context of the invention, this culture condition does not comprise to cultivate the cell pack on solidified (gelled) or liquid media, in suspension or in contact with any liquid environment which may hamper the necessary aeration as mentioned above. Since said cultivation is conducted essentially in the absence of any medium or liquid that surrounds each cell comprised by said cell pack, a sufficient relative humidity has to be assured. As will be appreciated by a skilled artisan, there is a stringent correlation between the density (in g wet cell weight per cm$^3$), the liquid content and the aeration (conferred to by the constitution of air voids in sufficient quantity and volume) of the cell pack. However, as will be explained in more detail hereinafter, the aerated cell pack may (temporarily) be treated by contacting the same with a small volume of transforming vectors or substances including but not limited to nutrients, substrates, hormones, enzymes, metabolites and precursors. In this context, temporarily means that these treatments including the provision of nutrients in the course of a long-term (i.e. for weeks or months) incubation are only performed during a short time period (up to 3 h, preferably up to 1 h), after which the liquid medium is withdrawn again and the air voids of the porous cell packs are reconstituted, resulting in a cell pack density as defined herein.

Accordingly, the method according to the invention optionally comprises to cultivate the cell pack in the presence of a gas, vapor, mist, dust, and/or aerosol etc. comprising or representing an organism, a chemical and/or biological substance or molecule, respectively.

According to a preferred embodiment, the cells comprised by the cell suspension culture are native (e.g. wild-type) or non-transgenic cells that, before performing the second cultivation step, are transformed with at least one expression vector comprising at least one heterologous nucleic acid sequence preferably being operably linked to a functional promoter, wherein said at least one heterologous nucleic acid sequence codes for a desired product to be accumulated and harvested in step (ii) of the method according to the invention.

The term "transformation" as used herein relates to the delivery of any nucleic acid or nucleic acid analoga into the plant cell. After transformation the nucleic acid may be stably integrated into the genome of the host cell. Alternatively, the delivered nucleic acid may not be integrated into the genome and may exert its effect either in the cytosol or in the nucleus or in any cellular organelle.

The nucleic acid may be an autonomously replicating element such as a viroid, a virus or deconstructed virus, or a combination of necessary elements from more than one virus. Alternatively, the delivered nucleic acid may only be a component of an autonomously replicating element such as a viroid, a virus or deconstructed virus. The other components may be provided/complemented by the host cell or by a transgenic host cell.

The term "heterologous" as used herein indicates that the gene/sequence of nucleotides in question have been introduced into plant cells by using genetic engineering. A heterologous gene may augment the expression of a protein of interest from an endogenous equivalent gene, i.e. one which normally performs the same or a similar function, or the inserted sequence may be additional to the endogenous gene or other sequence. A further possibility is for a nucleic acid sequence to be placed within a cultivated target cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression. Yet another possibility is for a nucleic acid sequence to induce silencing of an existing gene by antisense and/or silencing (desired product being the result to be achieved). Another possibility is for a nucleic acid with regulatory function such as a miRNA (desired product). Yet another possibility for is for a nucleic acid that is a ribozyme or an aptamer (desired product).

"Vector" is defined to include, inter alia, any plasmid, cosmid, phage, or viral vector in double or single stranded linear or circular form which may or may not be self transmissible or mobilizable, and which can transform a prokaryotic or eukaryotic host and exists extrachromosomally (e.g. autonomous replicating plasmid with an origin of replication).

"Expression vector" refers to a vector in which a nucleic acid is under the control of, and operably linked to, an appropriate promoter or other regulatory elements for transcription in a host cell such as a microbial or plant cell. The vector may be a bi-functional expression vector which functions in multiple hosts. In the case of genomic or subgenomic DNA, this may contain its own promoter or other regulatory elements and in the case of cDNA this may be under the control of an appropriate promoter or other regulatory elements for expression in the host cell. "Operably linked" means joined as part of the same nucleic acid molecule, suitably positioned and oriented for transcription to be initiated from a promoter.

A "biological vector" is any microorganism or virus capable of transforming a plant host cell, i.e. capable of delivering a nucleic acid into the plant cell. Examples for "biological vectors" are infectious microorganisms such as those belonging to *Agrobacterium, Radiobacter* and *Rhizobium* or viruses such as tobacco mosaic virus, potato virus x and cowpea mosaic virus. More specifically, *A. tumefaciens* is a "biological vector".

For the transformation of the cells, a suspension of a biological vector or a mixture of different biological vectors containing the genetic information is applied to the cell pack generated as outlined above. The vector infects the plant cells and transmits the genetic information. Due to the spongy structure of the plant cell material in the form of a cell pack, the vector can get access to the individual target cells just by capillary forces with no special treatments like injection or vacuum infiltration which are needed for reaching the cells in intact leaves or plants being necessary. Also, the loose and porous nature of the cell pack results in a large surface area accessible to the vector and thus enables high transformation efficiencies. This is different to callus material and differentiated plant tissues where the cells have much tighter cell-to-cell contacts resulting in limited access of the vector to the cell surface and thus in lower transformation efficiencies and product accumulation. Typically, more than 50% of the cells within a cell pack are transformed, which is substantially higher than in prior art. While no detailed data about transformation efficiencies were reported in U.S. Pat. No. 6,740,526 B1, it has been found that the method as disclosed therein is inferior to the cell pack methods according to the invention (see e.g. example 1, FIGS. 6C, 6D). This finding is additionally supported by the observation that 10- to 100 fold higher antibody yields could be achieved (see e.g. example 1). The vector suspension can easily be applied, e.g. by simple dropping or spraying. However, large and/or thick cell packs and certain user-defined shapes may require vacuum- or pressure-assisted application and removal of the biological vector suspension in order to achieve the desired cell pack density as defined herein. In contrast to the vacuum-assisted infiltration of leaf-tissue the described method has the advantage that excess biological vector suspension can be removed and reused and that the porous nature of the cell pack can be re-established immediately. The viability of infiltrated leaves depends drastically on the uptake and/or removal of the excess liquid to restore the gas-phase in the intercellular space. As this is difficult to control, vacuum-assisted infiltration of leaf-tissue suffers a higher variability and failure rate. The preferred embodiment is to apply the vector suspension to the cell pack as this has several practical advantages with respect to handling, automation, containment, up-scaling and waste production and removal. Alternatively, the suspension of the plant cells can be mixed with the vector suspension prior to forming the cell pack. The restoring of the air voids and the medium-deprived cultivation of a cell pack infiltrated with a biological vector like *Agrobacterium* ensures that the microbial vector does not destroy the plant cells by overgrowing them.

Instead of a biological vector suspension a solution containing nucleic acids or nucleic acid analoga, or a suspension of particles or an emulsion coated with or containing nucleic acids can be used.

After application of the biological vector, the cell pack is incubated or cultivated for a certain time under controlled conditions to allow the plant cell pack to re-establish its porous structure by restoring the air voids between individual cells or cell clusters and to allow the plant cells to express the recombinant proteins and thus to accumulate the desired product(s). The incubation conditions (e.g. time, temperature, humidity, light intensity) can be easily adjusted to favor the synthesis of a specific desired product. No special equipment is needed to support the cell pack, low-priced disposable plastic trays are sufficient for their maintenance. During a first period of cultivation the air voids reconstitute due to evaporation and absorption of the liquid applied with the biological vector. Alternatively, the air voids can be reconstituted by removing excess liquid by vacuum- or pressure-assisted methods. After cultivation is completed the cell packs are harvested and the product is separated/isolated from the biomass by applying appropriate purification procedures known in the art. In cases where an analytic or diagnostic result is meant to be the desired product, harvesting may also take place during the period of incubation/cultivation. The whole process can be automated and can be easily scaled up or down. Due to the easy set-up and lack of complex methodology, it is feasible to design this highly controlled process to fulfill GMP requirements and/or high-throughput applications and/or industrial large-scale production.

The method may be especially suited for products that are toxic to humans, animals and/or the environment, because the entire process can be performed under complete containment, therefore providing high biosafety. This applies also for compounds, vectors and/or nucleic acids used in the production process.

The term "harvested" as used herein is to be understood to comprise any action that is based on the expression and accumulation of the desired product. In addition to the harvesting comprising separation/isolation of the desired product as mentioned above, harvesting in general is also related to secure any diagnostic or analytical result that is based on the natively or recombinantly accumulated desired product. It is clear for a skilled person that in these cases separation/isolation of the desired product itself may be omitted.

Alternatively, the cell pack can also be generated from a suspension culture comprising transgenic cells in order to increase the production of a desired product (e.g. recombinant protein, metabolite), e.g. by providing a component of a replicative system or a metabolic pathway or by down-regulating certain host factors.

According to a further aspect the invention provides plant cell material in the form of a medium-deprived, porous structured and non-tissue multilayer cell pack having a density between 0.1 and 0.9 g, preferably between 0.2 and 0.85, most preferably between 0.4 and 0.8 g wet cell weight per $cm^3$, obtained or obtainable by a method according to the invention as disclosed herein. With other words, the present invention provides plant cell material in the form of a medium-deprived, porous structured and non-tissue multilayer cell pack having a density between 0.1 and 0.9, preferably between 0.2 and 0.85, most preferably between 0.4 and 0.8 g wet cell weight per $cm^3$.

The cell pack can also be treated with or cultivated in the presence of precursors, inducers, hormones, stabilizers (e.g. compatible solutes), inhibitors, RNAi/siRNA molecules, signaling compounds, enzymes (e.g. pectinase), and/or elicitors in addition to or instead of the vector suspension, for the production of recombinant and/or endogenous (native) proteins or metabolites.

In a particular embodiment of the invention applied substances induce differentiation of the undifferentiated cells comprised in the cell pack. This can be achieved, for example, by application of hormones or defined combination of hormones, or by transformation of the cells with genes for transcription factors.

The cell pack can be treated repeatedly using any series and/or combination of vector suspensions, nucleic acid solutions or substances mentioned previously. This means that the method of this invention can essentially be reiterated as long as the porous nature of the cell pack is maintained and the air voids are restored after each treatment. In particular, this also includes the use of a mixture of different vector suspensions to simultaneously co-transform the cells of the cell pack with different nucleic acids.

The cell pack can also comprise more than one different species of cells and/or different clones and/or different transgenic and/or non-transgenic cell lines. Moreover, a heterogeneous cell pack may also comprise cells from different species or even kingdoms, essentially using the plant cells as porous support for co-culturing the other cells, e.g. yeast, fungi, animal and human cells.

In another preferred embodiment of the invention, the porous cell pack is used as a highly reproducible and homogenous support for assays evaluating growth and/or vitality of co-cultivated organisms, wherein said evaluation is meant to represent the desired product. Preferably, the cell pack is used to test and/or screen molecules (metabolites, peptides and/or proteins) that are produced by the cell pack for their activity against the co-cultivated organism. Such assays generally comprise the following steps, (1) a porous cell pack according to the invention is generated, (2) a compound, vector and/or nucleic acid is added to said cell pack and optionally said cell pack is incubated for a suitable period, (3) a selected area of said porous cell pack is inoculated with a second organism, (4) the inoculated porous cell pack is incubated under conditions that enable the second organism to grow and (5) the effects (desired products) of products synthesized in the cell pack on the second organism, as for example on growth and/or vitality, is evaluated after a suitable incubation time. The second step may be omitted, e.g. if a transgenic suspension cell line is used.

Accordingly, the present invention provides using the plant cell material obtained or obtainable by a method as disclosed herein and/or having a density as defined above for analytical or diagnostic purposes. For example, the cells comprised by the cell pack may be incubated in the presence of an organism or of a substance to be analyzed or diagnosed. Hence, the invention also provides a diagnostic or analytical tool comprising plant cell material in the form of a medium-deprived, porous structured and non-tissue multilayer cell pack as disclosed herein.

Accordingly, those skilled in the art will readily appreciate that cell packs according to the invention can also be used for detecting analytes in a sample that is brought into contact with the cell pack ("treatment"). Again, the treatment of the cell pack with the sample containing the analyte of interest is only conducted temporarily, i.e. within a short period of time (up to 3 hours). After the treatment the air voids have again to be reconstituted, i.e. the corresponding density and porosity of the cell pack has to be reinstated. The cell pack is then incubated in the absence of a continuous contact to any liquid or gelled/solidified media (supply of nutrients). The analyte being present in the sample may induce signal transduction, gene expression or any other event that leads to a measurable change of the cell pack or manipulation of the cells comprised by it. Measurable changes or manipulations include but are not limited to fluorescent reported proteins, fluorescent reporter molecules, enzymes, changes leading to cell death, generation of auto fluorescence, physiological or morphological changes that can be revealed by analysing the cell pack or incubating the cell pack with additional reagents that produce a detectable signal directly in the cell pack or in eluates, extracts or other samples derived from the cell pack. It is to be understood that both wild type and genetically engineered plant cells can be used, including stable transgenic cells and transiently transformed cells. In particular, the latter can be derived by a previous transformation treatment of a cell pack generated from wild type cells.

The cell pack according to the present invention is highly amenable to different kinds of manipulations. In contrast to cells or protoplasts in suspensions, the density of the cells in the cell pack is higher. Consequently, compounds (e.g. elicitors for metabolite production) can be applied more economically as lower amounts are needed to obtain the same effective concentration. In addition, application of highly concentrated substances is possible, which is extremely useful for bioconversion/biotransformation. An advantage compared to intact plants, plant tissue and/or callus is the higher accessible cell surface area, which is due to the porous and fluffy structure of the cell pack and its loose cell contacts. Compared to both suspension cultures and intact plant tissues substances can be more easily and efficiently applied to and also removed from the cell pack. For example, precursors or toxic compounds can be applied for only a short period and pulse chase experiments can be conducted. Inducers can be applied in a more controlled and timely defined manner, allowing further refinement of optimal gene expression and other product accumulation conditions. A series of precursors and substrates can be applied sequentially to achieve complete conversion and to elucidate metabolic pathways. Moreover, accumulated secreted products can be harvested by simply washing the cell pack with a suitable buffer solution. Interestingly, this allows the repeated removal ("milking") of products to avoid product degradation and/or feedback inhibition. This strategy may also be utilized to avoid and/or reduce detrimental effects on the host cells, thereby maximizing productivity.

The provision of volatile substances, including nutrients (e.g. ammonia, carboxylic acids, sulfur dioxide, hydrogen sulfide, phosphines and organic amines) to the cell pack also has several advantages over currently established systems. Delivery of such substances in gaseous form is difficult to achieve for suspension cell cultures. The gas first needs to be dissolved in the solution, a process that is limited by solubility and transport. When using intact plants and plant tissues, again transport is a problem, but even more importantly, much larger incubation volumes need to be used and controlled. While this has been done for research purposes on small scales, large scale industrial applications are generally too expensive. Moreover, if the product itself is a volatile compound, control of the air pressure can be used to accumulate and/or harvest the product. Here, the higher cell density (i.e. cells per volume) compared to suspension cell cultures and the possibility for user-defined shapes and geometries offers unique possibilities, for example low-pressure cultivation, for process engineering that are not possible with any of the currently existing production systems. Hence the present invention provides an economical and scalable means for these types of applications.

Alternatively, dissolved compounds can be delivered to the porous cell pack in the form of an aerosol and/or mist and/or vapor. This mode of delivery is not possible for suspension cells. It is used for intact plants, however, the majority of the applied compound doesn't reach its target, requiring higher doses, volumes and number of treatments. The uptake of the compounds through the cuticula is very limited, requiring delivery through the stomata. Consequently, such applications are limited to highly effective compounds. Here, the present invention offers a way to efficiently deliver almost any compound in significant quantities to the cell pack.

Up-scaling can be implemented easily by parallelization, i.e. by simply generating the required number of cell packs. Alternatively, up-scaling can also be done by using suitably dimensioned large cell packs or sheets, columns or similar 3D structures.

The vertical size of a cell pack is only limited by the force which acts on the cells at the bottom of the pack and the resulting compaction of the pores. This problem, however, can be addressed by using intermediate supports. Accordingly, typical vertical sizes of a cell pack according to the invention range from a few mm, i.e. 3 to 5 mm, to several cm, i.e. 3 to 15 cm, or even more. The horizontal size is not limited. Dimensions from 10 $mm^3$ to 10 $m^3$ are feasible. Sufficient aeration/gas exchange has to be ensured, e.g. to maintain appropriate oxygen and carbon dioxide levels. Also accumulation of volatile primary and secondary metabolites has to be controlled, as e.g. high levels of ethylene can be detrimental for the cells. For cell packs of small thickness (about 3-5 cm) gas exchange by diffusion is usually sufficient. Thicker cell packs may require active aeration and/or integration of additional air channels. In this respect the present invention provides unique solutions because the suspension cells can be casted into virtually any user-defined shape.

According to a preferred embodiment, the desired product is selected from the group consisting of endogenous (i.e. native) and heterologous proteins or polypeptides, secondary metabolites, markers, and analytic/diagnostic results.

Genes of interest include those encoding proteins which themselves are natural medicaments such as pharmaceuticals or veterinary products.

Heterologous nucleic acids may encode, inter alia, genes of bacterial, fungal, plant, non-plant or animal origin. Proteins that can be produced in a process of the invention include heterodimers, such as FSH, immunoglobulins, fusion antibodies, single chain antibodies and other antibody formats or derivatives.

Such proteins include, but are not limited to retinoblastoma protein, p53, angiostatin, and leptin. Likewise, the methods of the invention can be used to produce mammalian regulatory proteins. Other sequences of interest include proteins, hormones, such as follicle stimulating hormone, growth factors, cytokines, serum albumin, hemoglobin, collagen, thaumatin, thaumatin-like proteins, epidermal growth factors such as VEGF, insulin, monomeric or dimeric or secretory immunoglobulin A, transferrin or transferrin fusion proteins, and receptors such as CD16, CD32, CD64, CD89, neonatal Fc-receptor.

As will be appreciated by the skilled artisan, the invention enables to produce a large variety of desired products such as proteins and polypeptides including (recombinant) proteins of pharmaceutical relevance (such as e.g. vaccines, antibodies, therapeutical enzymes, allergens and hypoallergens, antimicrobial peptides, structural proteins such as elastin and collagen for use as biocompatible coating materials, virus-like particles, protein bodies etc.), (recombinant) proteins of nutritional value (food and feed additives), (recombinant) proteins for diagnostic applications (such as e.g. enzymes, antibodies and engineered antibodies, other enzymes or fluorescent fusion proteins, antigens to be used as positive controls, binding ligands for protein arrays), and (recombinant) proteins of technical relevance (such as e.g. binding ligands for affinity sorbents, high value enzymes, biocatalysts).

Accordingly, the invention thus also provides a method for the production of at least one desired product preferably selected from the group consisting of native or heterologous proteins or polypeptides, secondary metabolites, markers, and analytic/diagnostic results. The method comprises the generation of a medium-deprived, porous structured and non-tissue multilayer cell pack having a density between 0.1 and 0.9, preferably between 0.2 and 0.85, most preferably between 0.4 and 0.8 g wet cell weight per $cm^3$, from a plant cell suspension culture, the application of a solution, suspension and/or a gas to the cell pack suitable to induce or alter the production of the desired product, the adjustment of the cell pack's density within the range as indicated above, if necessary, and the cultivation of the cell pack under a relative humidity of 50 to 100% to allow the cell pack to produce and accumulate the desired product. Optionally, the method further comprises to harvest or isolate the accumulated desired product from the producing cells comprised by the cell pack.

The cell pack based system of the invention is also suitable as a screening platform for molecular evolution, protein engineering, metabolic engineering and synthetic biology applications and, amongst others, enables optimization of the gene expression cassettes, plasmids etc. as used or intended to be used. Furthermore, by using cell packs as described herein, the invention provides an analytical method for evaluating gene expression constructs and engineered target proteins in a high through-put, highly reproducible and automatable manner. According to the invention and as mentioned before, the target of these applications is to gather information and results which as such represent desired products that are 'harvested' during the second cultivation period.

According to another aspect, the invention provides for the manipulation of post-translational protein modifications via transient expression of the involved enzymes and thus enables e.g. the modification of the glycosylation pattern of glycoproteins. Moreover, endogenous enzymes can be knocked down via silencing (e.g. glycosyltransferases, proteases, ubiquitin ligases) to effect product quality and quantity.

Furthermore, the invention provides for the production of secondary metabolites as desired products via transient expression of the involved pathway enzymes and/or their transcription factors. The biochemical pathways can also be manipulated by blocking competing pathways and/or catabolism via silencing of the corresponding enzymes. Likewise, the system according to the invention is well suited for improved metabolite production from genetically unmodified (native) cell cultures by generating and cultivating cell packs as described herein. Eventually, the invention can also be used to cultivate a cell pack generated from a transgenic suspension cell line harboring a constitutive promoter and/or an inducible promoter in the presence of a corresponding inducer.

Generally speaking, heterologous nucleic acids may be expressed by any appropriate process used in the art or they may be transcribed or expressed as follows:

(i) transient expression of 'naked' DNA e.g. comprising a promoter operably linked to the heterologous sequence of interest;

(ii) expression from an expression vector, such as a replicating vector. Generally speaking, those skilled in the art are well able to construct vectors and design protocols for transient recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, Molecular Cloning: a Laboratory Manual: 2nd edition, Sambrook et al, 1989, Cold Spring Harbor Laboratory Press or Current Protocols in Molecular Biology, Second Edition, Ausubel et al. eds., John Wiley & Sons, 1992;

(iii) expression from a non-integrating vector;

(iv) expression from a delivered T-DNA.

It will be understood that these categories are not mutually exclusive, for instance because a non-integrating vector may also be an expression vector etc.

Methods for achieving such expression are discussed elsewhere herein.

Constructs can be introduced at relatively high copy number with strong promoters, and without the inherent moderating effect which may occur when selecting a stable transformant in which a construct is integrated into the genome. As a result the levels and concentrations of protein produced may far exceed those obtainable by use of methods for protein production in plant cell based systems of the prior art (transgenic suspension cultures or transient expression in suspension).

Thus in one aspect of the invention there is disclosed use of a transiently transformed plant cell capable of generating mRNA encoding a target protein generated by transcription from an introduced nucleic acid construct including the target nucleotide sequence operably linked to a promoter.

The "introduced nucleic acid" will thus include the heterologous nucleic acid sequence as a DNA sequence provided in the form of a construct that is capable of giving rise to the production of extracellular protein at an elevated level relative to the level of protein production normally associated with stable transgene expression of the said DNA sequence.

Thus in a preferred aspect of the invention, there is disclosed a method of achieving expression of an heterologous nucleotide sequence in a plant cell pack, which method comprises the step of introducing into a target cell at least a first nucleic acid sequence comprising a heterologous nucleotide sequence.

In one embodiment there is provided a method of generating at least an extracellular heterologous protein, which method comprises the steps of:

(i) transiently introducing into a target cell comprised by the cell pack a first nucleic acid comprising the nucleotide sequence coding for the heterologous protein,
(ii) causing or permitting expression from the nucleic acid, over a period of time, of the heterologous protein by providing appropriate cultivation conditions, and
(iii) harvesting the accumulated heterologous protein from the producing cells.

The isolation may be by entirely conventional means, and may or may not entail partial or complete purification.

The time period for the cell pack cultivation may be any period up to or even beyond which the cell material remains viable, or until it is saturated with product; in general it may be preferred that it is between about 1 to 10 days, more preferably between about 1 to 6 days.

Naturally, those skilled in the art will recognize that more than one gene may be used in the, or each, construct. Multiple vectors (each including one or more nucleotide sequences encoding heterologous protein of choice) may be introduced into the target cells as described herein or elsewhere. This may be useful for producing e.g. multiple subunits e.g. of an enzyme or e.g. multiple enzymes of a biochemical pathway. This may also be useful to e.g. simultaneous knock-down endogenous genes, e.g. via siRNA mediated gene silencing and/or knock-in heterologous enzymes for post-translational modification of the product and/or the expression of markers and/or the production of multiple products of the same or of different types.

As shown in the examples below, transient expression of the heterologous sequence when introduced in this way can give high levels of target polypeptide over the course of the second incubation period, which will generally be several days, depending on the precise methods and materials employed. By using the methods of the invention as herein described, heterologous polypeptide accumulation is achieved.

Thus, transient expression in the cells comprised by the cell pack represents a useful tool in many contexts for which it may previously have been considered unsuitable e.g. dependable expression of unstable, that is, transiently expressed heterologous protein or polypeptide sequences that are accumulated within the producing cells.

The method may be particularly preferred in those applications where high levels of expression are required, but where viral constructs (with the requirement for plant 'infection') or stable transgenic plants are undesirable e.g. where a rapid assay is important, or where the sequence in question imparts a lethal or undesirable phenotype.

The reporter can be any detectable protein, such as a marker gene, commonly used in the art such as GUS, fluorescent proteins such as GFP or DsRed, luciferase etc. Preferably, the reporter is a non-invasive marker such as DsRed or luciferase. According to a further aspect of the invention, the plant cell material in the form of a medium-deprived non-tissue multilayer cell pack obtained or obtainable according to the method of the invention as described herein is used for analytical purposes. For example, the cells comprised by the cell pack can be incubated in the presence of a substance to be analyzed. For example, a cell pack generated form a transgenic suspension cell line containing a screenable marker gene (GFP, DsRed, Luciferase, GUS, secreted alkaline phosphatase, or an enzyme that is able to produce a detectable compound intracellularly) operably linked to an inducible promoter can be used to detect the inducer in test samples. Alternatively, the inducible reporter gene expression construct can also be transformed into a cell pack generated from a wild type (non-transgenic) suspension cell line in a first step and the test samples are then analyzed in a second step. Preferable, an incubation time of 1-5 days is carried out between the two steps. Then a suitable volume of a liquid test sample or a liquid extract of a non-liquid test sample is applied to the cell packed. It is important to ensure at that step that the porous structure of the cell pack is maintained by either using an appropriate ratio of the volume of the test sample and the weight of the cell pack or by removing excess liquid of the test sample after a suitable contact time. Suitable contact times are 1 min to 2 h, preferably 5 min to 1 h, more preferable 10 to 30 min. Suitable volumes of the liquid test samples are up to 0.75 ml per gram of the cell pack, preferable 0.5 ml per gram of the cell pack, more preferably 0.4 ml per gram of the cell pack.

Examples of inducible promoters include but are not limited to estrogen-, ethanol-, sugar-inducible promoter. Those skilled in the art do also understand that genetic circuits using repressors and depression can equally be used. For example, binding of tetracycline to the tet-repressor leads to derepression of the tetracycline promoter.

According to a preferred embodiment the present invention provides methods which are very useful to study and optimize recombination events, because of the ease of manipulation, high transformation efficiency and the numerous possibilities to deliver nucleic acids and/or compounds into the cells of the cell pack.

As will be appreciated by the skilled artisan, the cell pack according to the present invention is superior over leaf based transient systems, transient systems in liquid culture, wild type and/or stable transgenic suspension culture and the use of wild type and/or transgenic whole plants or parts thereof.

In contrast to the invention, leaf-based transient expression systems employ differentiated plant tissue consisting of different cell types (heterogeneous), whereas suspension cells are known to be dedifferentiated or undifferentiated. Compared to leaf-based systems, the invention provides the following advantages:

No space consuming growth facilities for biomass production necessary;
Independent of external climatic conditions;
No risk of plant pathogen infestation;
Rapid supply of large amounts of highly homogeneous biomass—this is of particular importance for pharmaceutical products (diminishes regulatory concerns);
Harvesting of the biomass is much easier (no need of special harvesting equipment);
Preservation by freezing and/or drying is easier due to a lower volume-biomass ratio;
Easier processing of the biomass and easier purification of the product (less lignin, less fibers, less host proteins, less pigments);
Biomass is produced under highly controlled aseptic conditions (diminishes regulatory concerns);
Speed advantage compared to whole plants, easy scale-up of the biomass (a 0.1 l starter-culture can be scaled-up in 15 days to provide 100 kg of biomass in a 1000 l suspension culture; 5d 2.5 l→5 d 50 l→5 d 1000 l);
Better space-time yields/space utilization (biomass per $m^2$; production and incubation usually requires no illumination, which allows a dense stacking of the cell packs);

Lower volumes of biological vector suspensions are required for infecting the same amount of biomass (less "waste" compared to tank infiltrations);

Implementation of a full containment easier than with leaf- and plant based methods;

Application of the bacteria or viruses is easier with the "cell pack" method;

Unintended post-transcriptional silencing triggered in an individual cell is confined to the few neighboring cells connected by plasmodesmata and does not spread systemically;

Additional chemical compounds (e.g. elicitors, inducers, hormones or precursors for metabolite production) can be applied more easily and more economically;

Possibility to elute only secreted proteins from the packed cells (less host proteins, access to only fully processed secreted proteins);

Due to the containment also hazardous products can be produced (high biosafety level);

High throughput screening possible (multiwell filter plates);

More flexible user-defined sizes and shapes can be realized;

More amenable to automation;

Highly homogeneous plant cell material that can be used for standardized growth assays of plant pathogens or other organisms, enabling high-throughput screening and Design-of-Experiments approaches;

The possibility of easily combining different methods, technologies and manipulation steps in a single format, simultaneously and/or sequentially.

The advantages in comparison to transient systems in liquid culture can be summarized as follows:

Increased expression of the transiently delivered transgenes compared to suspension cultures in bioreactors (shake-flasks or in fermenters) or to calli grown on solid media;

No need to control or suppress the bacterial growth to avoid overgrowing of the plant cells (antibiotics, auxotroph strains);

Use of "cell packs" allows a higher Agrobacteria to plant cell ratio compared to bioreactor-suspension;

Since the cells in the cell pack are not agitated, a more intimate vector-to-cell contact is achieved and there is no shearing;

Due to the high concentrated biomass in the second cultivation phase or period lower amounts of expensive compounds are needed (e.g. inducers (acetosyringone), hormones, precursors for metabolite production etc.);

The second cultivation phase occurs outside of the bioreactor that is used for production of the plant cells. This enables e.g. the use of continuous fermentation strategies in the first cultivation phase to assure constant supply of suspension cells. This results in a better and more economical utilization of the relative expensive bioreactor and enables higher capacities;

Due to the porous structure of the cell pack, limitation of oxygen supply is less critical.

Compared to the use of transgenic plants, the system according to the invention enables to recover a desired product more rapidly and offers a complete containment with no environmental concerns or risks and ensures no commingling with the food chain.

In comparison to the use of stable transgenic suspension cells, the invention provides for higher speed from gene to product, higher productivity, and enables the production of toxic products which may hamper the regeneration of a stably transformed cell line.

The invention will now be further described with reference to the following non-limiting Figures and Examples. Other embodiments of the invention will occur to those skilled in the art in the light of these.

DETAILED DESCRIPTION

Example 1

Comparison of Transient Expression in Cell Packs with Transient Expression in Suspension In order to evaluate the transient recombinant protein production in a cell pack according to this invention, transient expression of DsRed and the antibody 2G12 in an *Agrobacterium*-infiltrated cell pack was compared with the prior art method of co-cultivating suspension cells with *Agrobacterium* in liquid culture.

Figure 2:
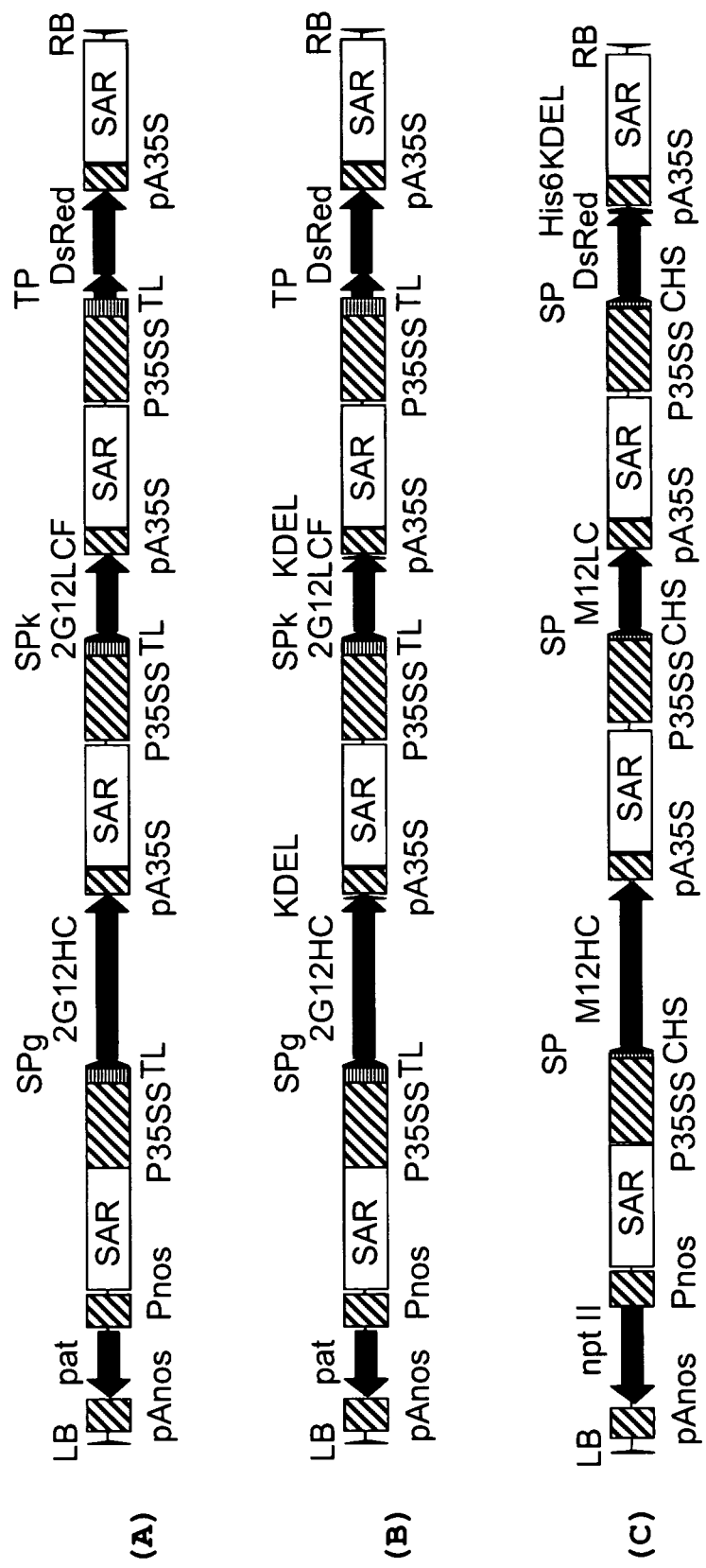
FIG. 2 depicts the T-DNA regions of expression vectors of the pTRA series containing sequences of different antibodies. (A) pTRAp 2G12F-Ds for co-expression of 2G12 antibody heavy chain, 2G12 antibody light chain and plastid targeted DsRed; (B) pTRAp 2G12F-Ds for co-expression of ER-retained 2G12 antibody heavy chain, ER-retained 2G12 antibody light chain and plastid targeted DsRed; (C) pTRAk MTAD for co-expression of M12 antibody heavy chain, M12 antibody light chain and ER-retained DsRed. SPg, signal peptide of human Ig gamma chain; 2G12HC, human anti-HIV-1 gp120 Ig 2G12 gamma heavy chain; SPk, signal peptide of human Ig kappa chain; 2G12LCF, human anti-HIV-1 gp120 Ig 2G12 kappa light chain; pat, phosphinothricin acetyltranferase; M12HC, human Ig M12 gamma heavy chain; M12LC, human Ig M12 lambda light chain. (see also FIG. 1)

Recombinant *Agrobacterium* (strain GV3101::pMP90RK) harboring the binary vector pTRAp-2G12FER-Ds containing the expression cassettes for heavy chain and light chain of a human antibody (2G12) and an expression cassette for a plastid targeted red fluorescent protein (DsRed) on the same T-DNA were used. Both 2G12 genes contain the KDEL sequence for ER-retention of the antibody (FIG. 2B). The KDEL sequence was deliberately used to avoid secretion of the antibody allowing a direct comparison of the productivity of cell pack and suspension cells.

*Agrobacterium* strains for transient transformation were prepared as follows. Cultures were initiated from glycerol stocks by inoculating 50 µl in 5 ml YEB-medium (5 g/l beef extract, 1 g/l yeast extract, 5 g/l peptone, 0.5 g/l MgSO$_4$, pH 7.4, supplemented with 50 mg/l carbenicillin and 25 mg/l kanamycin). The bacterial cultures were grown at 26° C. for three days to an optical density (OD) of approximately 5. The bacteria were pelleted by centrifugation and resuspended to OD 1 with infiltration medium (50 g/l sucrose, 2 g/l glucose, 0.5 g/l Ferty® 2 Mega (Planta Düngemittel, Germany), pH 5.3, supplemented with 200 µM acetosyringone). The bacterial suspension was then incubated for 1 hour at 22° C. before application.

Cells of Nicotiana tabacum L. cv. bright yellow 2 (BY-2) were cultivated in liquid medium (3% sucrose, 4.3 g/L Murashige and Skoog salts, 100 mg/L inositol, 1 mg/L thiamine, 0.2 mg/L 2,4-dichlorophenoxyacetic acid, 200 mg/L $KH_2PO_4$, pH 5.6) in the dark on a rotary shaker (180 rpm) at 26° C. Cells were subcultured weekly into fresh medium using a 4% inoculum.

Plant cells and Agrobacterium were handled under aseptic conditions using sterile equipment. A 50 ml aliquot of a 4 day old 400 ml BY-2 suspension culture was poured into a 75 ml Büchner funnel equipped with a 5.5 cm diameter cellulose filter (MN615) and the culture medium was completely removed by applying a vacuum (approximately 500 mbar for 1 min). The resulting cell pack was transferred into a petri dish and the fresh cell weight (FCW) was determined (weight=4.5 g, diameter=5.5 cm, height=0.3 cm, density=0.63 g/cm$^3$). Then 2.5 ml Agrobacterium suspension of OD 1 (0.55 ml per gram cell pack) was dropped uniformly onto the cell pack resulting in a complete infiltration. The amount of applied liquid was adjusted such that the cell pack was evenly moistened but not completely flooded to allow a fast recovery of the air voids. The agro-infiltrated cell pack was cultivated for 5 days at 26° C. and 95% relative humidity (RH) in the dark.

For co-cultivation 2.5 ml and 5 ml Agrobacterium suspension of OD 1 were added to 50 ml BY-2 suspension culture, giving the same and the double Agrobacterium-to-plant cell ratio as in the cell pack.

Figure 5:
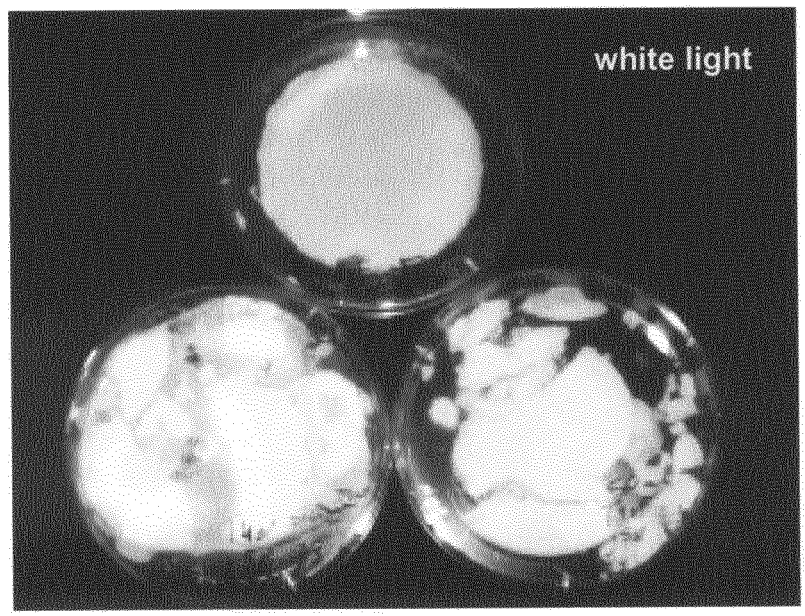
FIG. 5 shows macroscopic photos of BY-2 cells 5 days after infection with an *Agrobacterium* containing the expression cassettes for heavy chain and light chain of a human antibody (2G12) and a expression cassette for a plastid targeted red fluorescent protein (DsRed) under white light (A) and under green excitation light for visualization of DsRed fluorescence (B). Top: infiltrated "cell pack". Bottom: harvested suspension cells from co-cultivation with *Agrobacterium* at a final OD of 0.05 (left) and at a final OD of 0.1 (right).
Figure 5:
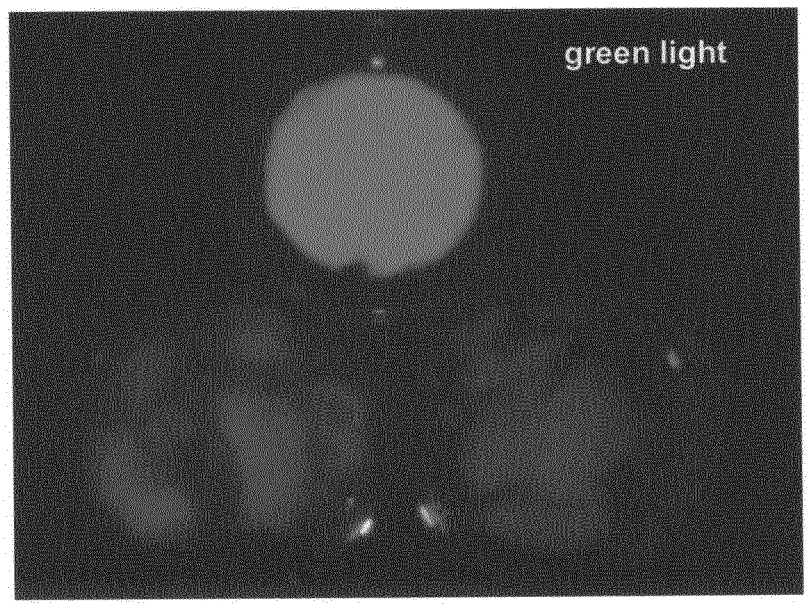
Figure 6:
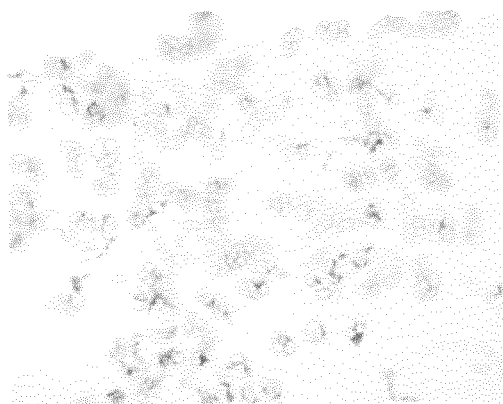
FIG. 6 shows representative microscopic photos of BY-2 cells 5 days after infection with an *Agrobacterium* containing the expression cassettes for heavy chain and light chain of a human antibody (2G12) and a expression cassette for a plastid targeted red fluorescent protein (DsRed) under white light (A,B) and under green excitation light for visualization of DsRed fluorescence (C, D). Cells from an agro-infected "cell pack" (A,C). Suspension cells from co-cultivation with *Agrobacterium* at a final OD of 0.1 (B,D).
Figure 6:
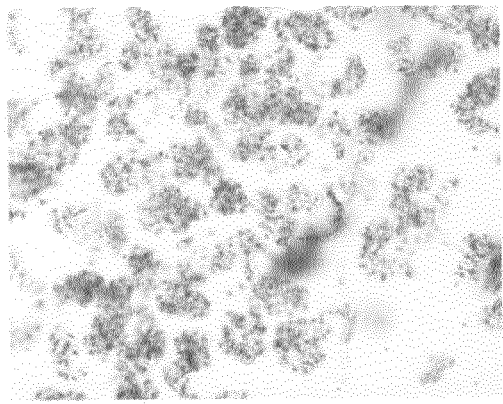
Figure 6:
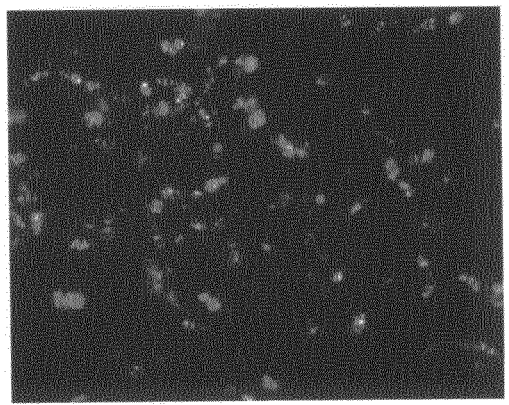
Figure 6:
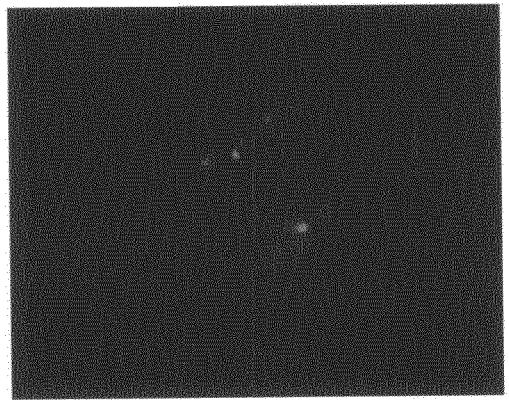

The co-cultivation cultures were cultivated on a rotary shaker with 180 rpm at 26° C. in the dark. The BY-2 cells from the co-cultivation cultures were harvested by vacuum filtration after 5 days and the resulting cell packs were transferred to petri dishes. The cells from both experiments were macroscopically inspected under green excitation light through a red emission filter for DsRed expression (FIG. 5). Red fluorescence was clearly visible in the agro-infected cell pack prepared according to the invention. Strikingly, no red fluorescence was visible in the cells that were co-cultivated with Agrobacterium in suspension. Microscopical analysis of the cells clearly showed that a much higher infection rate as well a higher DsRed expression per cell was achieved with the cell pack method according to the invention compared to the prior art method of co-cultivation in suspension (FIG. 6).

Soluble proteins were extracted from both approaches and DsRed and antibody accumulation was quantified. Briefly, cells were homogenized by sonication (Bandelin, Sonopuls, interval 0.9 s, 40 W, 2×30 sec) in two volumes (w/v) extraction buffer (50 mM potassium phosphate, 500 mM NaCl, 10 mM sodium bisulfate, pH 7.5). The cell debris was pelleted by centrifugation (15 min, 13000 g, 4° C.) and the clear supernatant was used for further analysis. DsRed was quantified by measuring the fluorescence (excitation 530±12.5 nm; emission 590±17.5 nm) of the extracted soluble proteins. Antibody quantification was performed by surface plasmon resonance spectroscopy using a BIACORE™ T200 instrument with protein A coupled to a CM5 sensorchip (as described in T. Holland et al., "Optimal nitrogen supply as a key to increased and sustained production of a monoclonal full-size antibody in BY-2 suspension culture", Biotechnol Bioeng 107: 278-289, 2010).

Neither DsRed nor 2G12 antibody was detected in extracts derived from co-cultivated suspension cells. In contrast, extracts derived from the agro-infected cell pack contained 55 µg DsRed and 47 µg 2G12 antibody per gram FCW.

This example shows that by using a cell pack according to this invention, substantially higher yields of recombinant proteins can be achieved by transient expression after co-cultivation with recombinant Agrobacteria in the cell pack as compared to the suspension culture. Moreover, this example clearly demonstrates that the higher productivity in the cell pack is due to a substantially higher transformation efficiency (typically 50%-80%) as well as to a higher product accumulation within the cell.

Example 2

Transient Expression of Plasmodium falciparum Antigens in Cell Packs

In order to test whether cell packs can be used for production of malaria antigens, different proteins of Plasmodium falciparum were transiently produced.

Figure 4:
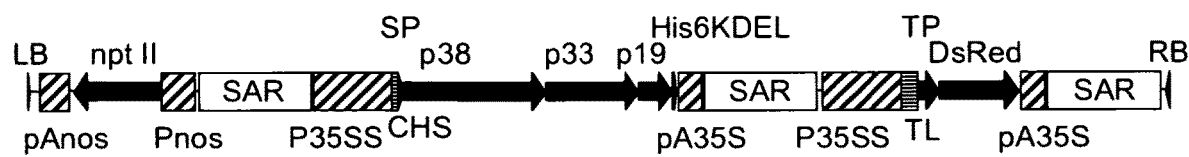
FIG. 4 depicts the T-DNA of the expression pTRAkc Msp1(383319)ERH-Ds containing a fragment of the *Plasmodium falciparum* 3D7 merozoite surface protein 1 (GenBank XM_001352134).

A recombinant Agrobacterium strain containing a binary vector with an expression cassette for an ER-retained carboxy-terminal fragment of Msp1 (p38, p33 and p19) from Plasmodium falciparum and a second expression cassette for a plastid targeted DsRed (FIG. 4). The bacteria were grown and prepared as described in Example 1. The Agrobacterium infiltration suspension was serial diluted from OD 1 to OD 0.0625 before infection of the plant cells.

Figure 7:
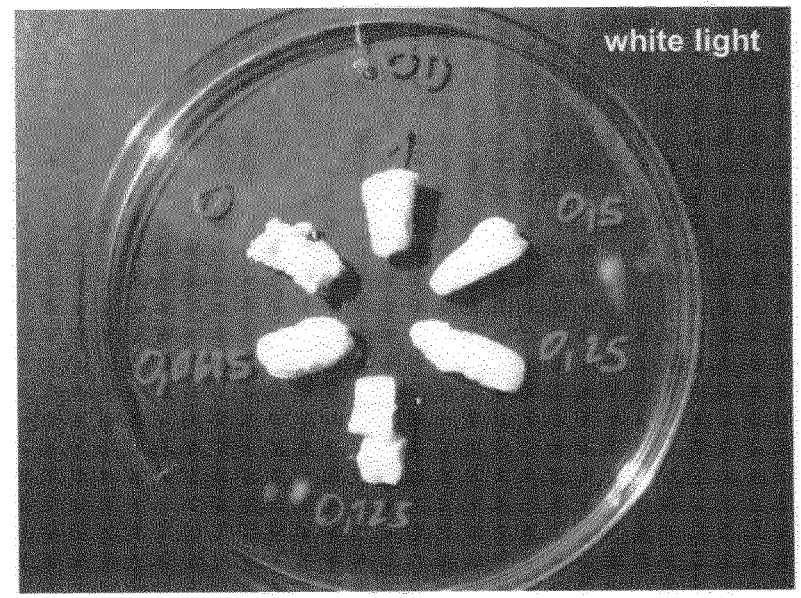
FIG. 7 shows photos of BY-2 cell packs 6 days after infection with Agrobacteria containing an expression cassette for a *Plasmodium falciparum* Msp1 fragment (p38-p33-p19) and an expression cassette for a plastid targeted DsRed under white light (A) and under green excitation light for visualization of DsRed fluorescence (B). The different optical densities (1, 0.5, 0.25, 0.125, 0.0625) are indicated on the petri dish (A). (C) shows the immunodetection of Msp1-p19 from *Plasmodium falciparum* via dot-blot.
Figure 7:
Figure 7:
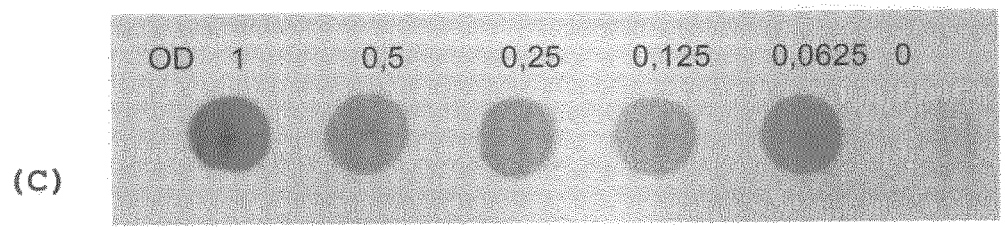

A 3 day old BY-2 suspension culture was used to generate a cell pack as described in Example 1. The cell pack was cut into pieces of approximately 5 mm×5 mm×10 mm (FIG. 7A). Six pieces were transferred into a petri dish and drop-infiltrated to saturation (approx. 150 µl per cell pack) with Agrobacterium suspensions of different optical densities. The negative control was infiltrated with infiltration medium only (FIG. 7). After 6 days of incubation at 20° C. and 95% RH the pack pieces were analyzed for DsRed fluorescence and antigen expression. DsRed was macroscopically observed under green excitation light through a red emission filter (FIG. 7B). For detection of the Plasmodium protein the soluble proteins were extracted as described in Example 1 and an aliquot of each extraction was dotted onto a nitrocellulose membrane. The presence of the Plasmodium protein was visualized by immunodetection using the monoclonal antibody 5.2 against the p19 domain and an AP-conjugated secondary antibody followed by incubation with NBT/BCIP (nitro-blue tetrazolium/5-bromo-4-chloro-3'-indolyphosphate).

A strong DsRed fluorescence was detected in all infected cell packs (FIG. 7B). Only minor difference in fluorescence intensity were detected between cell packs infiltrated with a Agrobacterium concentration of OD 1 and cell packs infiltrated with a more than 10-fold diluted Agrobacterium suspension of OD 0.0625. The clear immunological detection of the co-transformed Plasmodium protein in all infiltrated cell packs did also not reflect the 10-fold dilution of the Agrobacterium (FIG. 7C). The highest accumulation level was obtained by infiltration with an Agrobacterium suspension of OD 1.

In additional experiments other proteins from Plasmodium falciparum (Pfsp25 alone and in fusion with DsRed; and another fusion protein consisting of domains from several different malaria proteins) were successfully expressed in different BY-2 cell pack formats (data not shown). This example shows that recombinant protein accumulation is high even when the cell pack is infiltrated with lower amounts of Agrobacteria. The invention therefore provides a method for a more economical production which is particularly important for industrial applications on large scales. This also shows that different malaria proteins can be efficiently expressed and produced and that the disclosed method is generally suitable for the development and production of malaria vaccines and vaccines against other infectious diseases.

Example 3

Using Cell Packs for Screening Applications

Figure 1:
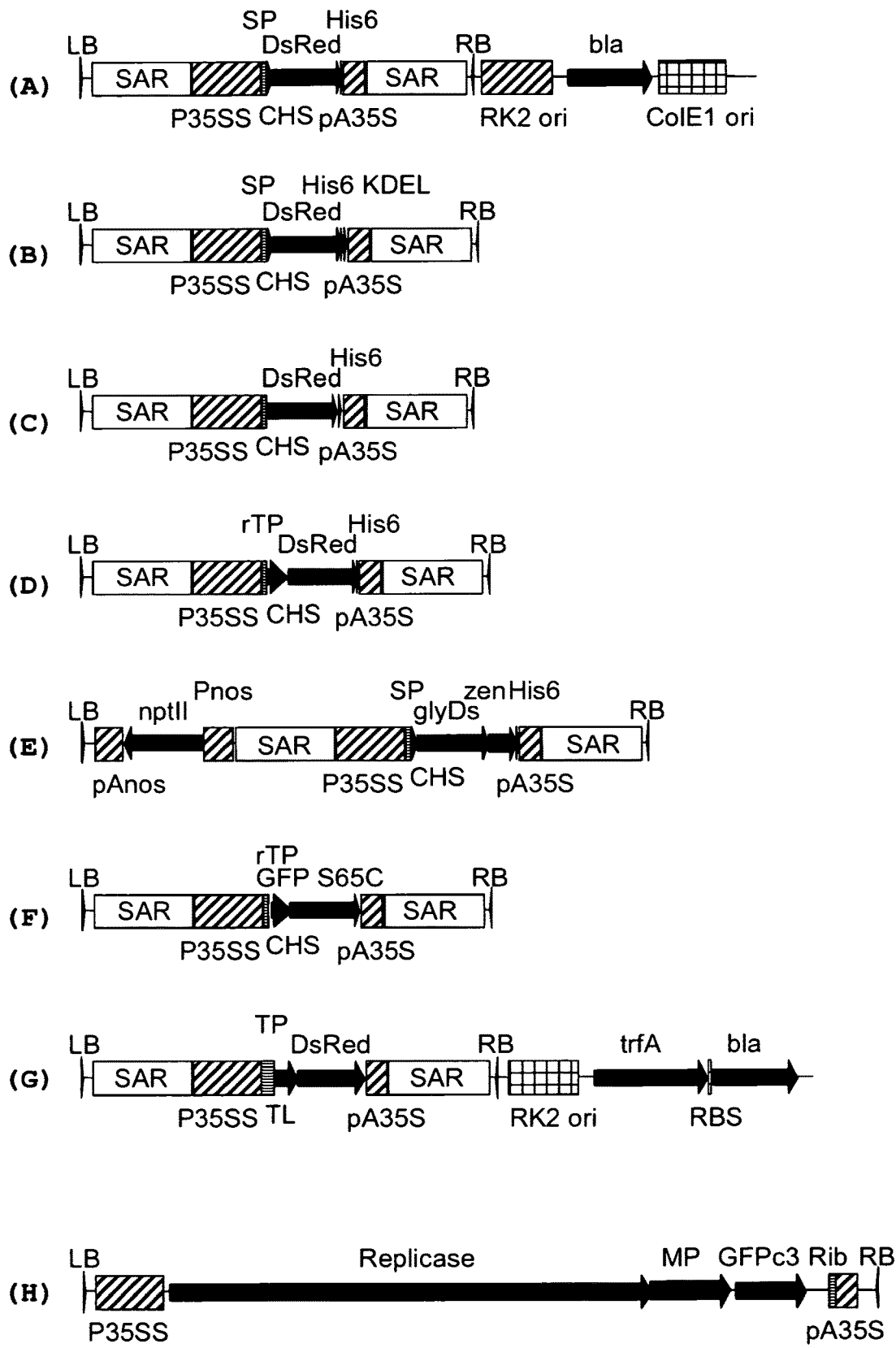
FIG. 1 depicts the T-DNAs from expression vectors based on the pTRA, pUTA and TRBO series containing sequences of different fluorescent proteins with different targeting signals. (A) pTRAc rfp-AH for expression of a secreted DsRed, (B) pTRAc rfp-ERH for expression of an ER-retained DsRed, (C) pTRAc rfp-H for expression of a cytosolic DsRed, (D) pTRAc rTPrfp-H for expression of a plastid targeted DsRed, (E) pTRAkc glyDS-zenH for expression of a protein body targeted DsRed, (F) pTRAc rTPgfp for expression of a plastid targeted GFP, (G) pUTA TPrfp for expression of a plastid targeted DsRed, (H) TRBO-G for expression of a cytosolic GFP using a tobacco mosaic virus replicon. The vector backbone of pTRA is based on pPAM (GenBank AY027531). The vector backbone of pUTA contains the replication initiation protein trfA for host strain independent plasmid replication from the RK2 ori. The backbone of TRBO originates from pCB301 (GenBank AF139061). LB and RB, left and right border of the T-DNA; SAR, scaffold attachment region; P and pA, 35S-promoter with duplicated enhancer and terminator of the cauliflower mosaic virus (CaMV) 35S gene; CHS, 5'-UTR from chalcone synthetase gene (*P. hortense*); TL, 5'-UTR of the tobacco etch virus (TEV); SP, codon-optimized signal peptide of the murine mAb24; TP, transit peptide of GBSSI from *H. vulgare*; rTP, transit peptide of GBSSI from *S. tuberosum*; DsRed, red fluorescent protein from *Discosoma* sp.; glyDs, DsRed variant with N-glycosylation site; zen, N-terminus of gamma-zein from *Zea mays*; GFP, green fluorescent protein from Aequorea Victoria (S65C mutant, cycle 3 mutant); RK2 or broard host range on of replication; bla, beta-lactamase gene; ColE1 ori, on of replication (*E. coli*); His6, histidin tag; KDEL, ER-retention tag; RBS, ribosomal binding site; Pnos and pAnos, promoter and terminator of the nopaline synthase; npt II, neomycin phosphotransferase gene; Replicase, tobacco mosaic virus (TMV)126K/183K protein; MP, TMV movement protein; Rib, Ribozyme.
Figure 8:
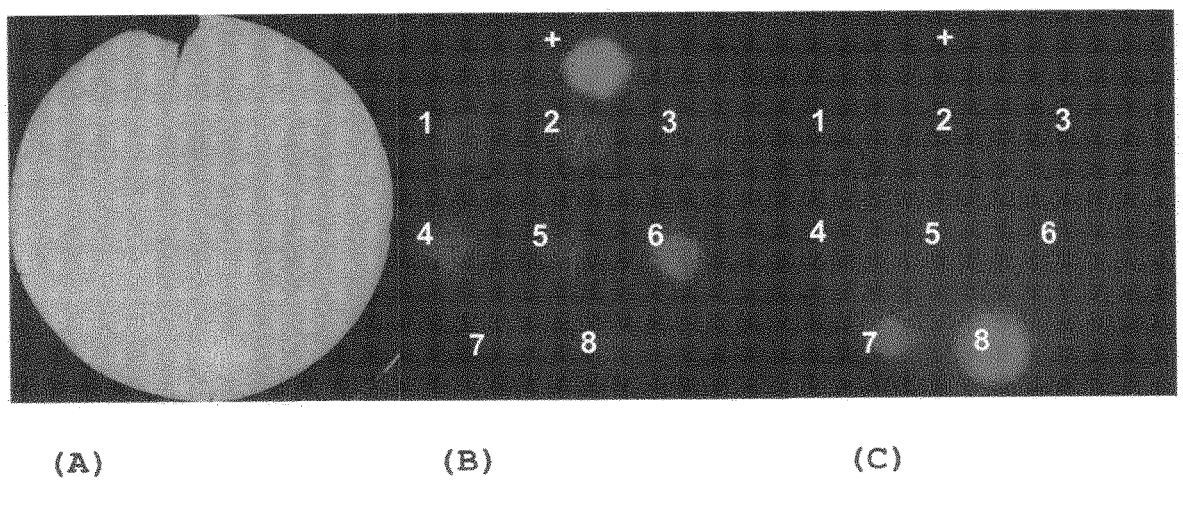
FIG. 8 shows photographs of a flat BY-2 cell pack 4 days after different *Agrobacterium* strains were dotted on the cells under white light (A), with a GFP filter set (B) and with a DsRed filter set (C). (1-3) three clones of EHA105 Agrobacteria transformed with pTRBO-G, (4-6) three clones of GV2260 Agrobacteria transformed with pTRBO-G, (7) EHA105 containing pUTA-TPrfp, (8) GV3101::pMP90RK containing pUTA-TPrfp and (+) positive control GV3101::pMP90RK containing pTRA-rTPgfp.

Since cell packs are highly homogeneous they are also ideal for screening purposes. Therefore, this was demonstrated in this example by evaluating the influence of the employed *Agrobacterium* strain and different expression vectors on transient product accumulation. Two different expression vectors were used. The binary vector pUTA-TPrfp which contains a 35S-promoter driven plastid targeted DsRed (FIG. 1G), and the binary vector pTRBO-G which contains a 35S-promoter driven cDNA of tobacco mosaic virus (TMV) where the coat protein sequence is replaced by GFP (FIG. 1H)(J. A. Lindbo, "TRBO: a high-efficiency tobacco mosaic virus RNA-based overexpression vector", *Plant Phys* 145: 1232-1240, 2007). Each vector was introduced into two different *Agrobacterium* strains. The standard vector pUTA-TPrfp was introduced into GV3101::pMP90RK and EHA105; the viral vector pTRBO-G into GV2260 and EHA105 (R. Helens et al., "A guide to *Agrobacterium* binary Ti vectors", *TIBS* 5: 446-451, 2000).

pTRA-rTPgfp in GV3101::pMP90RK was used as positive control (FIG. 1F). Liquid cultures of GV-pUTA-TPrfp, EHA-pUTA-TPrfp and GV-pTRA-rTPgfp were initiated from glycerol stocks. For GV-pTRBO-G and EHA-pTRBO-G cultures, three unchecked colonies obtained from a freshly made electro-transformation with plasmid DNA were inoculated for each strain. *Agrobacterium* strains were grown under standard condition (Example 1) with 50 mg/l carbenicillin and 25 mg/l kanamycin for GV-pUTA-TPrfp, GV-pTRBO-G and GV-pTRA-rTPgfp, 50 mg/l carbenicillin for EHA-pUTA-TPrfp and 25 mg/l kanamycin for EHA-pTRBO-G. After 3 days the bacteria were pelleted by centrifugation and resuspended to OD 1 with infiltration medium. The bacterial suspensions were incubated for 3 hours at 22° C. before application. A cell pack (weight=4 g, diameter=5.5 cm, height=0.3 cm, density=0.56 g/cm$^3$) was generated using 25 ml of a 5 day old BY-2 culture grown under standard conditions (Example 1). The cell pack was placed upside-down in a petri dish and then 40 μl of each *Agrobacterium* suspension was dotted on the smooth surface. The infiltrated cell pack was incubated at 26° C. with 95% RH. After 4 days the cell pack was inspected under blue excitation light through a green filter for GFP expression (FIG. 8B) and under green excitation light through a red filter for DsRed expression (FIG. 8C). Fluorescent protein expression with the viral vector as well as with the standard binary vector was clearly less efficient when EHA105 was used for transferring the expression constructs into the plant cells. This result was confirmed by infecting 3 g cell packs in columns and by transient transformation of *Nicotiana benthamiana* leaves with the same *Agrobacterium* suspensions (data not shown). This easy to handle small scale "agro-dot" method can also be used to evaluate other parameter which can influence target protein expression (e.g. growing conditions and pretreatment of the Agrobacteria, infiltration media composition or cultivation conditions of the infiltrated cell pack). Hundreds of samples can by analyzed in parallel without demanding technical equipment, a 1 L shake flask with 400 ml BY-2 culture will provide material for 16 times 4 g cell packs in 5 days, from a 11 day old 400 ml culture 30 cell packs can be generated.

Example 4

Transient Expression in Cell Packs in Columns

In order to test whether it is possible to generate, infiltrate and maintain cell packs in columns, several experiments were performed. In this example differently targeted versions of the red fluorescent protein DsRed and the green fluorescent protein GFP were transiently expressed in a column format of packed cells.

Different *Agrobacterium* strains harboring binary expression vectors for a secreted DsRed (FIG. 1A), an ER-retained DsRed (FIG. 1B), a cytosolic DsRed (FIG. 1C), a plastid targeted DsRed (FIG. 10), a protein body targeted DsRed (FIG. 1E) and a plastid targeted GFP (FIG. 1F) were used. The *Agrobacterium* suspensions for agro-infection were prepared as described in Example 1. Before application the bacterial suspensions were incubated for 5 hours at 22° C. For co-infection experiments, two *Agrobacterium* strains (containing an ER-retained DsRed and a plastid targeted GFP, respectively) of OD 1 were mixed, giving a OD of 0.5 for each of the strains.

11 day old BY-2 suspension cells grown under standard conditions (example 1) were used to generate cell packs in two different types of sterile polypropylene columns. Micro spin-columns (Receiver Column 20 μm, MACHEREY-NAGEL, Germany, FIG. 8A) with a volume of 0.7 ml and midi columns (QIAGEN-tip 100 column, QIAGEN, Germany, FIG. 9B) with 14 ml volume, both equipped with a 20 μm polyethylene filter frit, were used. Cell packs were generated by pouring the suspension culture into a column connected to a vacuum. After the medium was completely removed by vacuum filtration, the dimensions of the resulting cell pack were determined. 1 ml of the suspension culture was used for the micro columns, giving a cell pack of 0.3 g weight with a diameter of 0.68 cm, a height of 1.5 cm and a density of 0.54 g/cm$^3$. Cell packs generated from 10 ml suspension in the midi columns had a weight of 3 g, a diameter of 1.4 cm, a height of 3.6 cm and a density of 0.54 g/cm$^3$.

The cell packs were infiltrated in the column by pipetting the *Agrobacterium* suspension onto the cell packs (1 ml per gram cell pack). In order to achieve a complete infiltration, a short vacuum was applied until the first liquid drops left the column but still leaving the top of the cell pack covered with suspension. After incubating the infiltrated cell packs for 30 min at 22° C. the remaining liquid was completely removed by applying vacuum to the column in order to restore the air voids. The removal of the applied liquid was controlled by determining the weight of the treated column packed cells. To ensure high viability of the cells during the following incubation phase, the weight increase due to liquid uptake by the cell pack or cells should preferably not exceed e.g. 15% of the original fresh cell weight (FCW) of the pack. The cell packs were cultivated in the columns at 26° C. and 92% relative humidity. 5 days after agro-infection total soluble proteins were extracted from the cell packs as described in Example 1.

Figure 9:
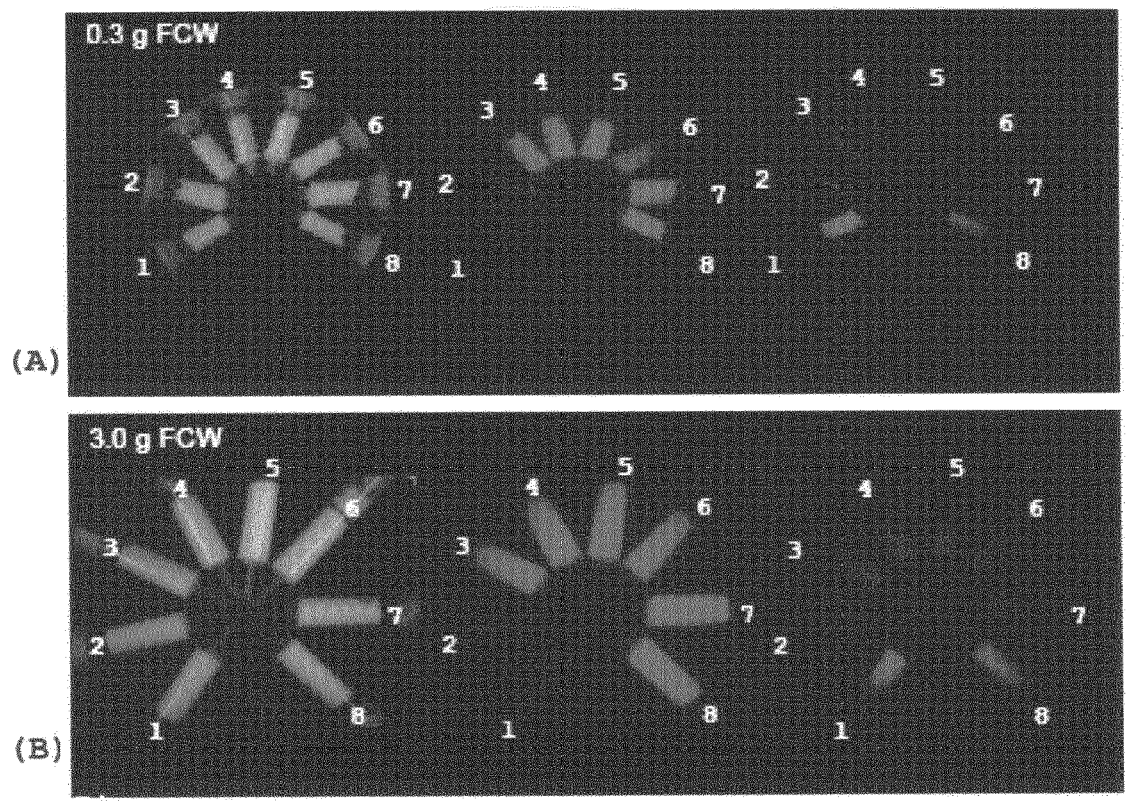
FIG. 9 shows the accumulation of differently targeted fluorescent proteins in cell packs 5 days after agro-infection. Cell packs of 0.3 g fresh weight in micro columns (A) and cell packs of 3 g in 14 ml columns (B) were transiently transformed. (1) plastid targeted GFP, (2) untransformed cells, (3) secreted DsRed, (4) ER-retained DsRed, (5) cytosolic DsRed, (6) plastid targeted DsRed, (7) protein body targeted DsRed, (8) co-transformation with ER-retained DsRed and plastid targeted GFP. The photos were taken under white light (left), with a DsRed filter set (middle) and with a GFP filter set (right). The extracted amount of DsRed is shown in (C).
Figure 9:
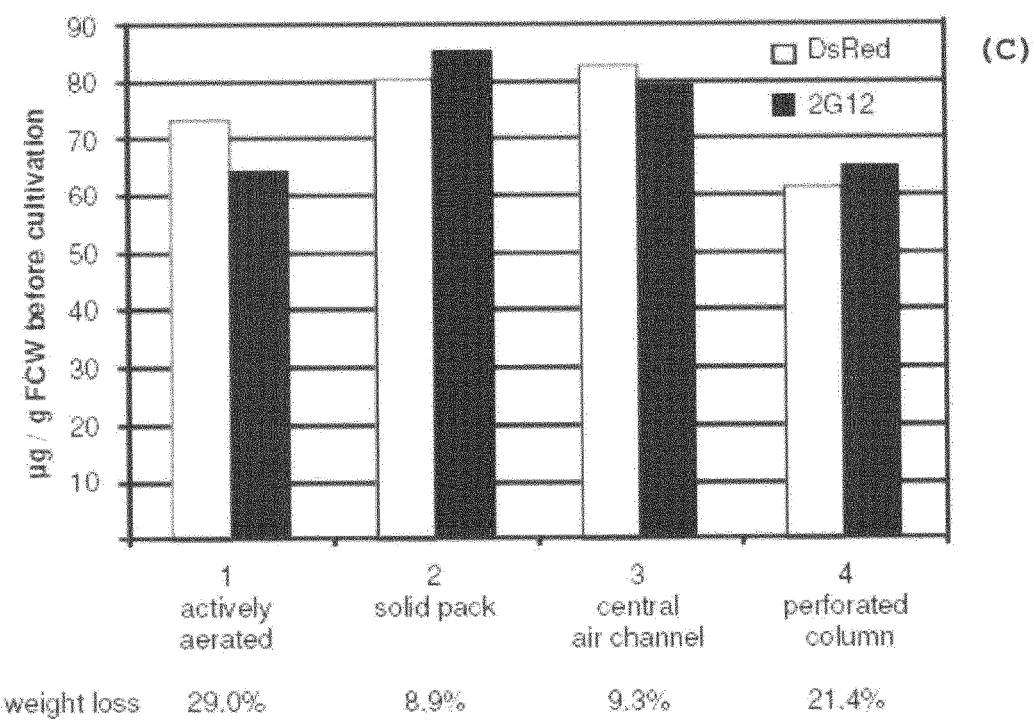
Figure 10:
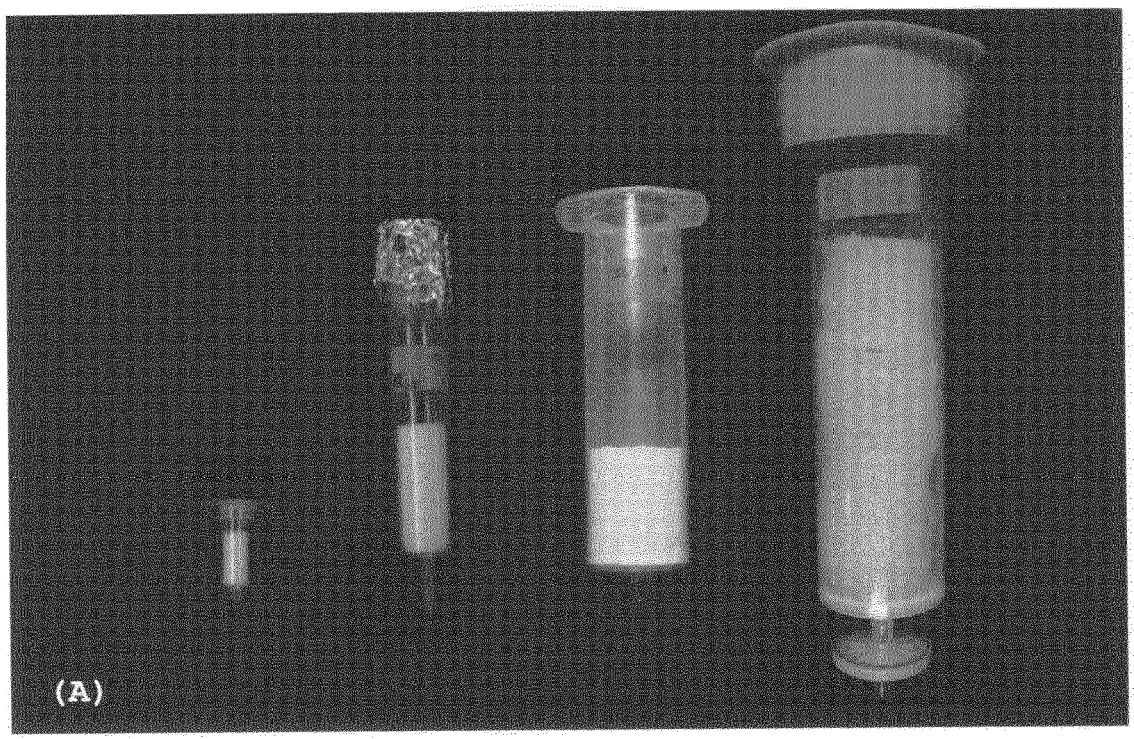
FIG. 10 shows photos of BY-2 cell packs in columns of different dimensions transiently expressing DsRed. (A) under white light, (B) with a DsRed filter set.
Figure 10:
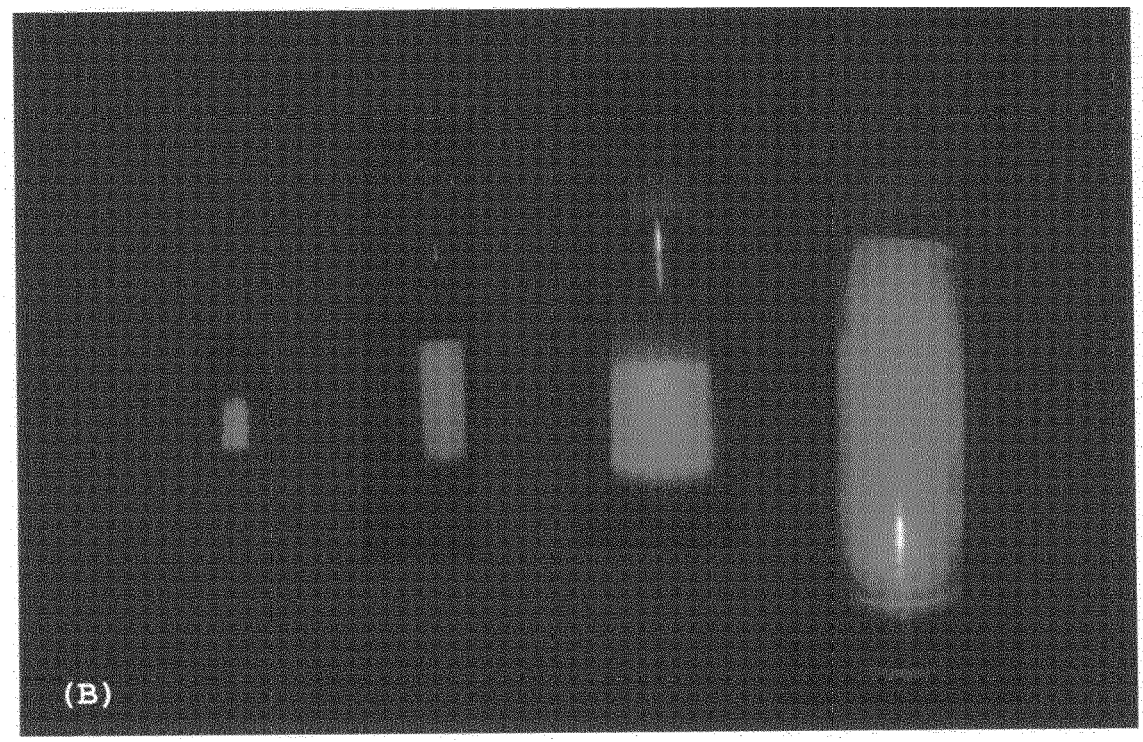

Fluorescent protein expression was macroscopically detectable in all infiltrated cell packs (FIG. 9) showing that different compartments of the cells in a cell pack can be used for recombinant protein production. The cell packs showed a homogeneous fluorescence indicating an efficient delivery of the Agrobacteria to each area of the cell pack. Depending on the target compartment clear difference in the accumulation levels were observed, ranging from approx. 40 µg/g FCW for a plastid targeted DsRed to approx. 160 µg/g FCW for a cytosolic DsRed (FIG. 9C). DsRed targeted into protein bodies showed a high fluorescence in vivo but was not extractable due to the insolubility of protein bodies. The simultaneous expression of DsRed and GFP (FIGS. 9A8 and 9B8) showed that co-infection with two separated *Agrobacterium* strains was possible. The cell pack size, 0.3 g in micro columns or 3 g in 14 ml columns, had no effect on the expression levels. Therefore, it is envisaged that micro cell packs are very useful for screening and analytical purposes, for example to determine the optimal parameters for a large-scale production (e.g. pre-culture, infection and co-culture conditions), to evaluate different expression constructs or to develop and study metabolic pathways. Due to the high homogeneity of the cell packs they are particularly useful for statistical designs and multivariate experiments. For high-throughput analysis 96 well filter plates are available which are compatible with automated systems (e.g. Receiver plate 20 µm, Chromabond® MULTI filter plate, both MACHEREY-NAGEL, Germany). The wells of these filter plates are similar to the micro columns used for generation and infiltration of cell packs in this example. Compared to high-throughput analysis in suspension cultures in 96 well plates micro cell packs have the advantage that transient expression is more efficient (see Example 1) and that more biomass is available for analysis. In addition to the columns used above, also larger columns were tested (FIG. 10). DsRed expression was observed 4 days after agro-infection in a 12 g cell pack (2.8 cm diameter, 3.5 cm height) in a 70 ml column (GenElute™ HP Plasmid Midiprep Kit filter syringe, SIGMA, USA) and in an 87 g cell pack (3.7 cm diameter, 11 cm height) in a 150 ml column (Chromabond® polypropylene column 150 ml, MACHEREY-NAGEL, Germany). The 12 g cell pack was generated from a 4 day old BY-2 suspension culture and infiltrated with an *Agrobacterium* harboring an expression construct for a plastid targeted DsRed (FIG. 2B). The 87 g cell pack was generated from an 11 day old culture and infiltrated with an *Agrobacterium* harboring an expression construct for an ER-retained DsRed (FIG. 1B). The only difference to the standard procedures described above was that the 87 g cell pack was infiltrated with an *Agrobacterium* suspension of OD 0.25. The determination of the density of the cell pack and the confirmation that sufficient liquid was removed to restore the air voids were achieved by weighing. The different experiments also showed that cells of different age, i.e. days after subcultivation, are suitable for generating a cell pack according to this invention. Moreover different shapes and sizes of cell packs are possible. This example shows that it is feasible to transform and incubate also larger cell packs under sterile and contained conditions. This is in contrast to leaf-based systems which are generally not sterile.

Example 5

Effect of Increased Aeration on Transient Protein Production

Figure 11:
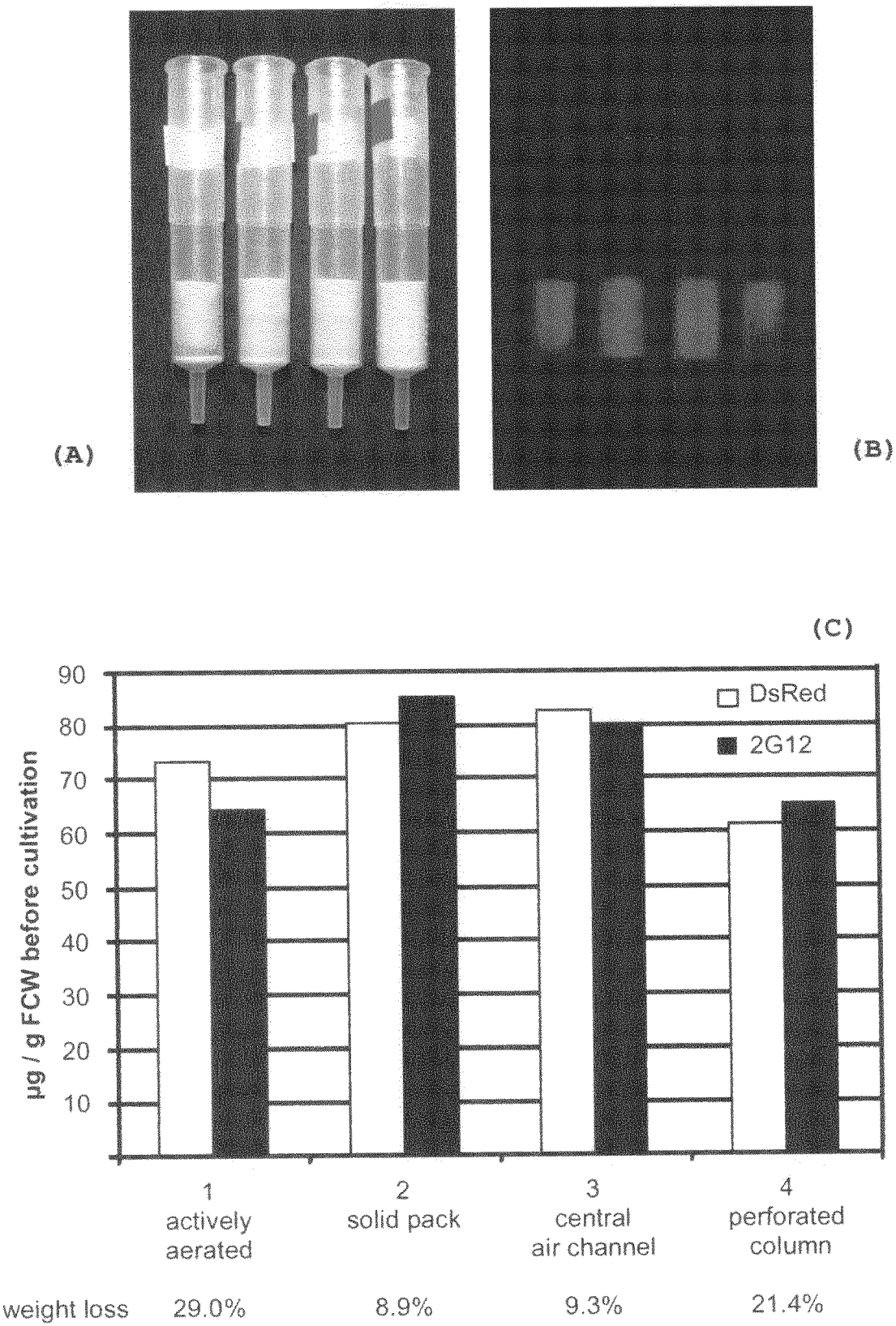
FIG. 11 shows the influence of the aeration conditions on the expression of transiently expressed DsRed and 2G12, respectively. (A, B) shows pictures of differently aerated cell packs in columns, (A) under white light, (B) with a DsRed filter set. (C) shows the accumulation levels of DsRed and 2G12 in column packed BY-2 cells 140 hours after agro-infection. The weight loss of the cell packs is indicated below the chart.

To investigate the influence of the aeration on the performance of transformed packed cells, different set-ups were tested: (1) an actively aerated cell pack, (2) a passively aerated cell pack, (3) a cell pack with a central air channel, (4) a cell pack in a perforated column (FIG. 11A).

The *Agrobacterium* strain harboring the binary vector pTRAp-2G12FER-Ds (FIG. 2B) was grown under standard conditions and prepared as described in example 1.

4.5 day old BY-2 suspension cells grown under standard conditions were used to generate cell packs in 14 ml midi columns (example 4). In experiments 1,2,4 solid cell packs were generated, the perforated column was sealed with Parafilm®. In experiment 3 a plastic stick with a diameter of 2.5 mm was placed in the center of the column. The cell packs had diameters of 1.4 cm and weights from 2.1-2.5 g, heights from 2.5-2.7 cm and densities of approximately 0.57 g/cm$^3$. After infiltration with *Agrobacterium* suspension and removal of the liquid (example 4), the stick from column 3 and the Parafilm® seal from column 4 were removed giving a cell pack with a central air channel and a cell pack with additional air supply from the sides, respectively. The columns were cultivated at 26° C. in an incubator with 92% RH. Column 1 was connected to an air pump, which was placed inside the incubator to the supply with air of 26° C. and 92% RH. The pump had a capacity of 50 l/h and was set to a periodical pumping (15 min on, 45 min off). 6 days after agro-infection the weight of the cell packs were determined and the soluble proteins were extracted from the cell packs and analyzed for DsRed and 2G12 antibody expression (as described in example 1). Because of the different weight loss of the cell packs, the amount of DsRed and antibody 2G12 was calculated based on the FCW at the start of the cultivation in the incubator (FIG. 11C). The results show that a loss of moisture due to evaporation either through forced aeration (FIG. 11C1) or an increased surface (FIG. 11C4), has a negative effect on the productivity of the packed cells. Both the accumulation of the plastid targeted DsRed as well the accumulation of the ER-retained antibody is reduced in cells showing a weight loss of more than 20%. Therefore, cultivation conditions, which minimize desiccation of the cell packs should be used (e.g. by increasing the relative humidity or by remoistening the cell packs). On the other hand, the results show that at this dimension aeration is sufficient and measures for better oxygen supply and gas exchange are not needed.

Example 6

Non-Destructive Harvest of Secreted Products from Packed Cells

To determine whether recombinant secretory proteins can be eluted without destroying the cells, BY-2 suspension cells were packed in columns and transiently transformed via agroinfection. Different *Agrobacterium* strains containing expression constructs for a secretory monoclonal antibody M12 together with an ER-retained DsRed (FIG. 2C), a secretory DsRed (FIG. 1A), ER-retained DsRed (FIG. 1B) and a protein body forming DsRed (FIG. 1E), respectively, were used for the experiment. The M12 antibody (150 kDa) and the DsRed (108 kDa) are examples for large secreted proteins. Since the ER-retained DsRed is intracellular, it is a suitable control to examine whether the plant cells are disrupted during incubation or elution. The insoluble protein body forming DsRed was employed as a control for whole cell extracts.

Figure 12:
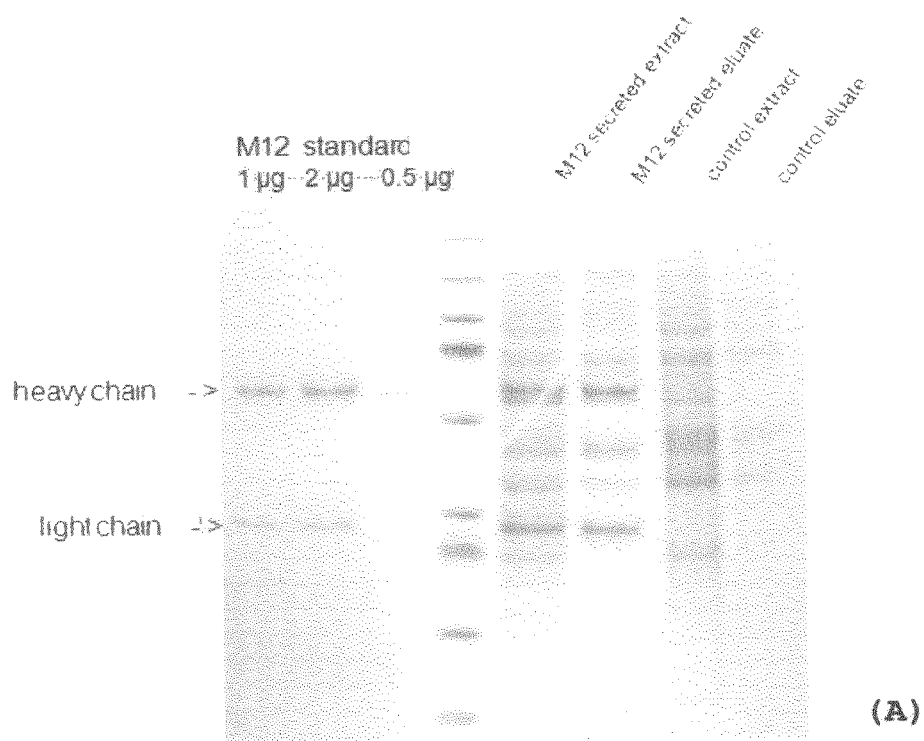
FIG. 12 shows Coomassie-stained SDS-PAGE gels of total extracts and eluates of column packed cells 5 days after infiltration with transgenic *Agrobacterium*. (A) Infection with expression constructs for a secreted M12 antibody or a protein body forming DsRed (control). (B) Infection with expression constructs for a secreted or ER-retained DsRed. The extract samples on the gels correspond to approx. 10 mg fresh cell weight (FCW), the eluate samples on the gel correspond to eluates from approx. 20 mg FCW.
Figure 12:
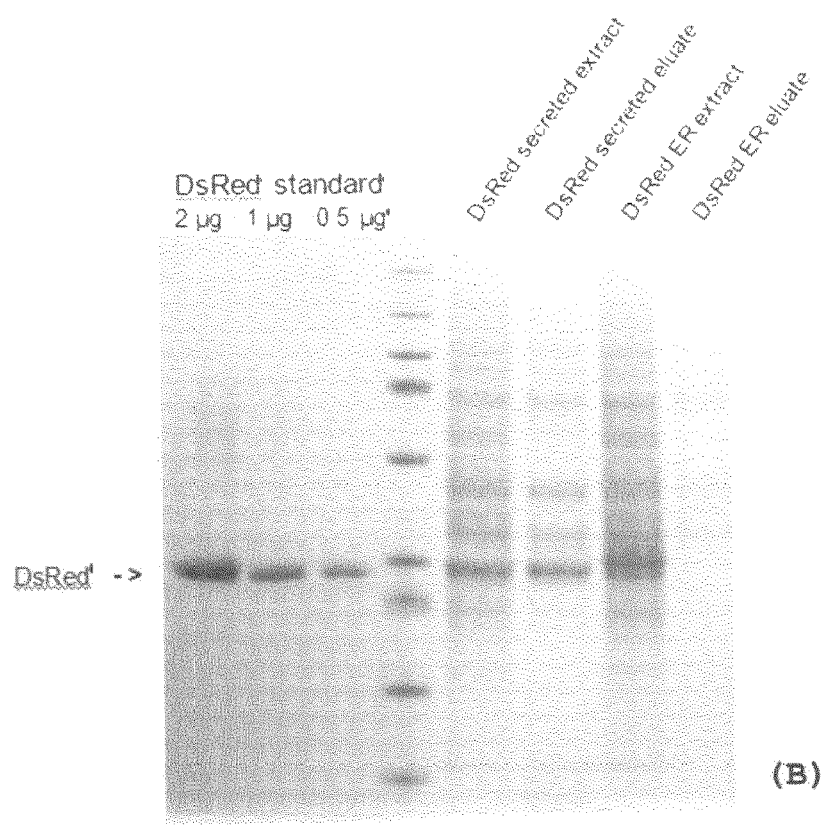

11 day old BY-2 suspension cells grown under standard conditions (example 1) were used to generate cell packs in columns. 10 ml of the suspension culture was poured into a 14 ml polypropylene column (diameter 1.4 cm, height 9 cm) equipped with a 20 µm polyethylene filter frit. The medium was completely removed by vacuum filtration and the resulting cell pack (weight=3 g, diameter=1.4 cm, height=3.6 cm, density=0.54 g/cm³) was infiltrated within the column by pipetting the *Agrobacterium* suspension onto the cell pack (1 ml per gram cell pack). In order to achieve a complete infiltration, a short vacuum was applied until the first liquid drops left the column but still leaving the top of the cell pack covered with suspension. The infiltrated cell pack was incubated for 30 min at 22° C. and then the remaining liquid was completely removed to restore the porous structure by applying vacuum to the column. The cell packs were cultivated in the columns at 26° C. and 92% relative humidity. 5 days after agro-infection the total soluble proteins from 200 mg FCW samples of the packed cells were extracted with 2 volumes of extraction buffer (50 mM potassium phosphate, 500 mM NaCl, 10 mM sodium bisulfite, pH 7.5). In order to only recover secreted proteins the remaining column packed cells were washed with extraction buffer as follows. 3 ml buffer was applied to a column and sucked into the cell pack by a short vacuum. After 30 min incubation the buffer was collected by vacuum and applied again onto the cells. After three consecutive washing steps 2.7 ml eluate was recovered and subsequently clarified by centrifugation. The total extractable protein preparations and the elutable proteins were analyzed for recombinant protein content on Coomassie-stained SDS-PAGE gels (FIG. 12). The protein amounts loaded on the gels corresponded to the total extractable proteins from 10 mg cell pack and to the elutable proteins from 20 mg cell pack. The intensities of the recombinant protein bands are almost the same in extract and eluate for the antibody (FIG. 12A) and for DsRed (FIG. 12B), respectively. This means that in both cases approximately 50% of the totally produced recombinant protein can be eluted. However the amount of contaminating host proteins was lower in the elution samples.

The amount of M12 antibody was quantified by surface plasmon resonance spectroscopy with protein A coupled to a sensorchip, the amount of DsRed was determined by fluorescence. Approximately 55% (96 µg/g FCW) of the totally produced secretory M12 (175 µg/g FCW) and 40% (28 µg/g FCW) of the secretory DsRed (70 µg/g FCW) were eluted. The presence of only a fraction (less than 1%) of the totally produced ER-retained DsRed (120 µg/g FCW) in the elution samples indicates that the cells were not damaged during cultivation or during elution of the secreted proteins (see also FIG. 12B).

When using the prior art method of transient transformation of plant leaves or whole plants a selective preparation of secreted products is feasible at an analytical scale by collecting intercellular washing fluid but impractical at a larger scale. Hence, at large scale secreted products have to be recovered from whole biomass extracts. Thus the desired product has to be purified from a complex mixture of host compounds (e.g. proteins, metabolites, lignins, celluloses). In particular, phenolic compounds are problematic regarding downstream processing and purification. In this respect the present invention circumvents these problems since secreted products can be directly eluted from the cell pack without destroying the plant cells and with a minimum of contaminating host compounds. Moreover, because of the scalability, the cell pack method can be implemented at a large industrial scale. It is conceivable that under optimized elution and cultivation conditions repeated elution of secreted products from packed cells will result in much higher yields of the desired product.

Example 7

Production of a Novel Secondary Metabolite by Metabolic Engineering

In order to establish a new biosynthetic pathway in packed cells the enzyme tryptophan decarboxylase (TDC; EC 4.1.1.28), which does not exist in *N. tabacum* was transiently expressed in BY-2 cell packs.

TDC is a cytosolic enzyme that catalyzes an early step of the terpenoid indole alkaloid biosynthetic pathway by decarboxylation of 1-tryptophan to produce the protoalkaloid tryptamine. Tryptamine is a common precursor of a group of therapeutically relevant secondary metabolites (e.g. the anticancer drugs vinblastine and vincristine from *Catharanthus roseus*). In order to further increase the yield of the desired metabolite the precursor tryptophan was fed in a second step to the cell packs after transformation.

Figure 3:
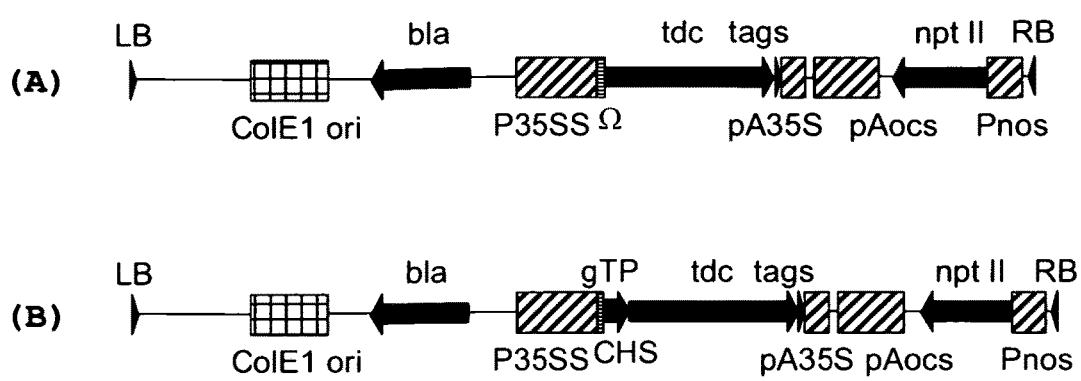
FIG. 3 depicts the T-DNA of expression vectors based on the pSS series containing sequences of tryptophan decarboxylase with different targeting signals (S. Di Fiore et al., "Targeting tryptophan decarboxylase to selected subcellular compartments of tobacco plants affects enzyme stability and in vivo function and leads to a lesion-mimic phenotype", *Plant Physiol* 129: 1160-1169, 2002). The vector backbone originates from pPCV002. (A) pT-CYT for expression of a cytosolic tryptophan decarboxylase (TDC); (B) pT-CHL for expressin of a plastid targeted TDC. Ω, 5'-UTR of the tobacco mosaic virus; tags, c-myc/His6 tags; pAocs, terminator of the octopine synthase. (see also FIG. 1, 2)

4 day old BY-2 suspension cells were packed in 14 ml columns as described in example 4 giving cell packs of 2 g FCW with a density of 0.58 g/cm³. The cell packs were transiently transformed in duplicate via agro-infection. *Agrobacterium tumefaciens* strain GV3101::pMP90RK transformed with plant expression constructs for either a plastid-targeted green fluorescent protein (GFP) (FIG. 1F), a plastid-targeted TDC (FIG. 3A) or a cytosolic TDC (FIG. 3B) were grown under standard conditions (example 1).

The *Agrobacterium* strains were pelleted by centrifugation, resuspended and adjusted to an OD of 1 with infiltration medium. The bacterial suspension was incubated for 4 hours at 22° C. before application onto plant cell packs.

Each cell pack was infiltrated with 2 ml *Agrobacterium* suspension, incubated for 30 min at 22° C., sucked dry by vacuum and cultivated further at 26° C. and 92% relative humidity. 18 hours after the agro-infection the cell packs were again infiltrated either with 2 ml tryptophan solution (50 mM in half concentrated infiltration medium) or with 2 ml half concentrated infiltration medium. After incubation of the infiltrated cell packs for 30 min at 26° C., the solutions were again completely removed by vacuum and the column packed cells were put back to the cultivation cabinet. Samples of approximately 250 mg FCW were taken at 69 h, 91 h and 112 h after agro-infection and stored at −80° C. Tryptamine was extracted and assayed according to the method of R. S. Sangwan et al., "Direct fluorometry of phase-extracted tryptamine-based fast quantitative assay of 1-tryptophan decarboxylase from *Catharanthus roseus* leaf", *Anal Biochem* 255: 39-46, (1998), with minor modifications.

In brief, water soluble compounds were extracted from the cell samples by sonication in 2 volume (v/w) extraction buffer (50 mM potassium phosphate, 500 mM NaCl, 10 mM sodium bisulfate, pH 7.5) (see example 1). After adding 0.9 ml distilled water to 0.1 ml of the cleared extract, 2 ml 5 M NaOH and 3.5 ml ethyl acetate was added. The emulsion was mixed by vortexing for 10 sec and placed at 4° C. for 16 h for phase separation. The upper organic phase was subjected to fluorometric analysis by using an Aminco Bowman AB2 luminescence spectrometer (Spectronic Instruments, Rochester, N.Y.). Tryptamine fluorescence was measured at 280 nm excitation and 350 nm emission wavelengths with 4-nm slit width for excitation and emission light and the photomultiplier voltage set to 575 V.

Figure 13:
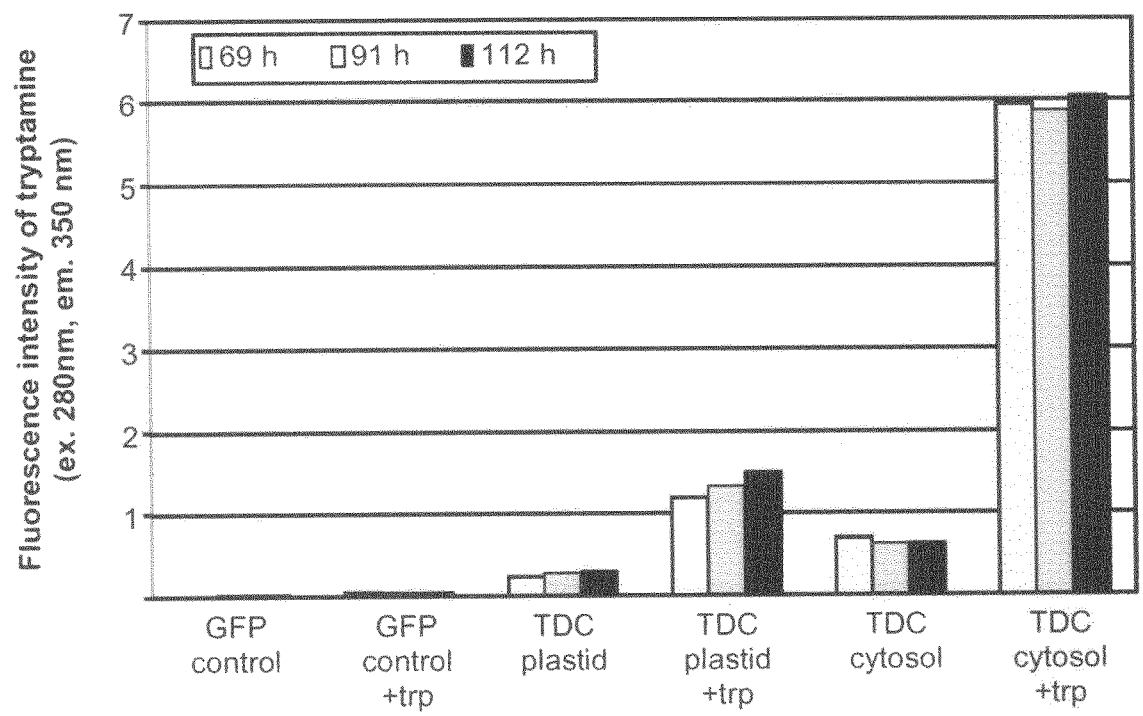
FIG. 13 shows the tryptamine accumulation in transiently transformed packed cells at different time points after agro-infection with differently targeted tryptophan decarboxylase or GFP. Additional tryptophan (trp) was added 18 h after agro-infection.

The detected tryptamine levels show that an active TDC was expressed in the plastids and in the cytosol, respectively (FIG. 13). The introduced enzymes converted endogenous tryptophan into the novel substance tryptamine. Feeding additional tryptophan to the transiently TDC expressing cells led to a clear increase in the production of tryptamine (5-fold for the plastid targeted TDC, nearly 10-fold for the cytosolic TDC).

This example also shows that the method according to the invention can be used for production of a metabolite.

Moreover, it demonstrates that a cell pack can not only be transformed to e.g. produce an enzyme (TDC) but also that substrates and/or precursors can easily be supplied to the cells in a subsequent step in order to increase the product yield. Therefore, the present invention also includes possibilities to deliver any substance of interest to the cells in order to optimize product formation (e.g. additional plant nutrients, inducers, inhibitors), e.g. by repeated transformation, infiltration and incubation steps. The manipulation of the cell metabolism can take place by, during, before and/or after delivering the genetic information by any combination of applying suitable compounds and genes.

Those skilled in the art will easily recognize that cell packs prepared from wild type, mutated and/or transgenic suspension cultures can also be manipulated without transformation, i.e. by applying different compounds. This in particular means that yields of naturally occurring compounds can be increased by using cell packs according to this invention and adding suitable substrates, hormones, inhibitors and/or precursors to them.

Example 8

Cell Packs from Suspension Cultures of Different Plant Species

In addition to *N. tabacum* BY-2 suspension cells, several other plant cell suspensions were used to generate cell packs.

*Catharanthus roseus*

Cells of *C. roseus* were cultivated in MS67 medium (3% sucrose, 4.4 g/L Murashige and Skoog salts, 0.6 mg/L thiamine, 0.2 mg/L kinetin, 1 mg/L 2,4-dichlorophenoxyacetic acid, pH 5.8) or in BY-2 medium (example 1) in the dark on a rotary shaker (180 rpm) at 26° C. Cells were subcultured weekly (20:100) into fresh medium.

*Arabidopsis thaliana*

Cells of *A. thaliana* were cultivated in ARA medium (3% sucrose, 4.4 g/L Murashige and Skoog salts, 0.5 mg/L naphtalene acetic acid, 0.1 mg/L kinetin, pH 5.7) with 16 h light/8 h darkness on a rotary shaker (180 rpm) at 26° C. Cells were subcultured weekly (15:100) into fresh medium.

*Nicotiana benthamiana*

Cells of *N. benthamiana* were cultivated in BY-2 medium (example 1) in the dark on a rotary shaker (180 rpm) at 26° C. Cells were subcultured weekly (20:100) into fresh medium.

Cell packs of different shapes were prepared from each suspension culture. For the experiments 4 to 5 days old cultures were used. Cookie-like cell packs of different thickness (0.2-0.5 cm) were generated as described in example 1. Cell packs from about 2 to 4 cm height were produced in 14 ml midi columns as described in example 4. Depending on the plant species, different densities of the cell packs were obtained. The density of *C. roseus* cell packs was typically 0.65-0.75 g/cm$^3$, *A. thaliana* cell packs had a density from about 0.55-0.67 g/cm$^3$ and *N. benthamiana* packs had a density from about 0.6-0.7 g/cm$^3$.

Cell packs of *C. roseus*, *A. thaliana* and *N. benthamiana* infiltrated with Agrobacteria harboring the binary vector pTRAp-2G12FER-Ds (FIG. 2B) showed macroscopically detectable DsRed expression. The production of the antibody 2G12 was also confirmed for each tested plant species by surface plasmon resonance spectroscopy as described in example 1.

Figure 14:
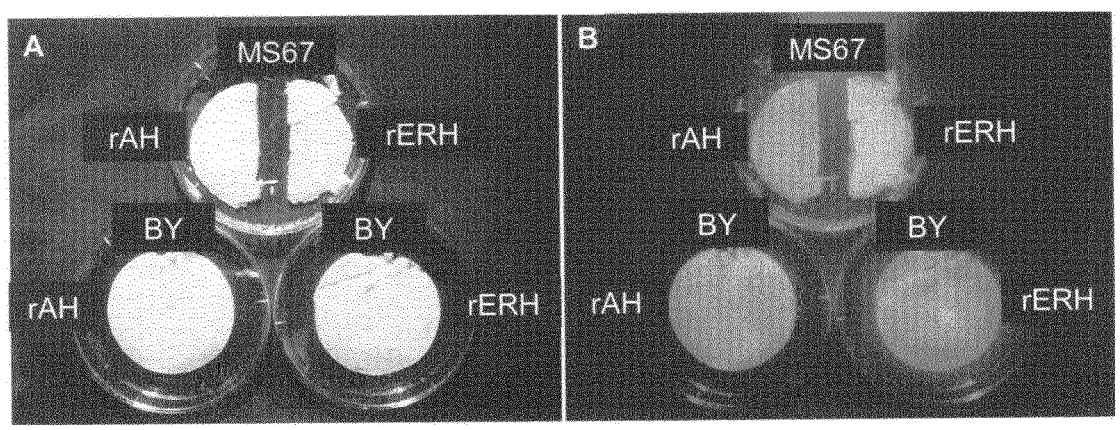
FIG. 14 shows photos of *Catharanthus roseus* cell packs generated from differently pre-cultivated suspension cultures days after infiltration with Agrobacteria containing plant expression vectors for either a secreted DsRed (rAH) or an ER-retained DsRed (rERH). The photos were taken under white light (A) and with a DsRed filter set (B). The suspension cells were grown in MS67 medium or in BY-2 medium, respectively.

Interestingly, depending on the medium used for the *C. roseus* suspension culture clear difference in the expression levels were observed. This was further analyzed by transforming *C. roseus* cell packs generated from cells grown in MS67 medium or BY-2 medium with two different DsRed expression constructs, pTRAc rfp-AH and pTRAc rfp-ERH (FIG. 1A,B). Both the secreted and the ER-retained DsRed accumulated much higher in cells which were grown in BY-2 medium (FIG. 14). This shows the importance of an optimization of also the pre-culture conditions to achieve high transformation and/or high product synthesis. The experiments showed that the present invention can be applied to plant cells from different species.

It is well known to those skilled in the art that culture conditions (e.g. temperature, aeration, stirring speed, light composition etc.) and/or culture medium composition (e.g. nutrients, hormones, pH, conductivity, osmolarity etc.) are determining factors for the morphological and physiological characteristics of a plant suspension culture. Variation of each factor can have influence on the performance of the plant cells in the subsequent steps. This means that culture conditions and/or medium compositions have to be optimized for any production. In addition to the optimization of the production of the starting material, the infiltration parameters (e.g. *Agrobacterium* density, contact time, infiltration medium composition) and the cell pack culture conditions (e.g. duration, temperature, aeration, feeding, application of additives) have to be optimized for any plant cell line and for any product.

Example 9

Using Packed Cells as a Substrate for the Cultivation of Pathogens

A 3.64 ml cell pack (weight=2 g, diameter=5.5 cm, height=0.15 cm, density=0.55 g/cm$^3$) was generated using 50 ml of a 4 day old BY-2 culture grown under standard conditions (Example 1). The cell pack was placed in an empty petri dish and infiltrated with 1 ml infiltration medium (50 g/l sucrose, 2 g/l glucose, 0.5 g/l Ferty 2 Mega (Planta Düngemittel, Germany), pH 5.3) which was completely taken up by the cell pack (weight of cell pack=3 g; density=0.825 g/cm$^3$). This amount of volume (i.e. less or equal to 1 ml per 2 gram of cell pack) has been found to be favourable for the start of incubation of cell packs in petri dishes because the air voids are regenerated within a few hours. This has been confirmed by control measurements of the density of the cell pack that decreased to less than 0.6 g/cm$^3$ due to evaporation. Importantly, higher amounts of liquid (i.e. more than 1 ml per 2 gram of cell pack) were highly detrimental because, due to the excess liquid, the air voids could not be reconstituted resulting in a cell pack having a density that was too high to appropriately support cell viability or even to prevent cell death.

Figure 15:
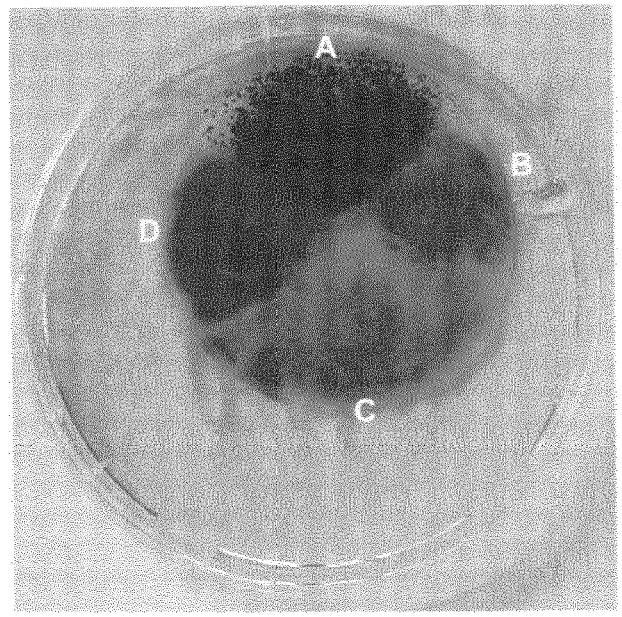
FIG. 15 shows a photograph of a BY-2 cell pack 11 days after spores of different *Aspergillus* species were spotted on the pack. (A) *A. niger*, (B) *A. nidulans*, (C) *A. flavus*, (D) *A. parasiticus*.

The next treatment step consisted of spotting a small volume of 20 µl of spore suspensions of four different *Aspergillus* species (FIG. 15; A-D) onto the surface of the cell pack. The cell pack was incubated for 11 days and then photographed (FIG. 15).

This example shows that the plant cell pack can be used as a growth substrate for different *Aspergillus* species. *Aspergillus* was selected as a representative as a plant pathogen but also as a representative as a human and animal pathogen.

In this example the cell pack was prepared from wild type BY2 suspension cells for subsequently cultivating the fungi. Those skilled in the art will appreciate that transgenic suspension cells can also be used. In particular, transgenic cell packs producing anti-fungal peptides, proteins or compounds can be used and their effect on the growth and development of the fungi can be studied. Equally, cell packs generated from wild type cells can first be subjected to a transformation treatment and then be used for studying the impact of the products on growth of the fungal pathogen. Those skilled in the art will also accept that the method can also be used for studying the impact of anti-bacterial compounds. The use of cell packs in multi-titre plates for high throughput screening applications is described in example 11 below and it is obvious that these examples can also be combined.

Example 10

Non-Destructive Harvest of a Secreted Product from Cell Pack Generated from a Transgenic Suspension Cell Line Transgenic BY2 suspension cultures were generated after transformation with an expression construct for a secretory monoclonal antibody M12 together with an ER-retained DsRed (FIG. 2C). After selection on plates containing kanamycin, transgenic calli were transferred to liquid medium to establish highly homogenous suspension cultures. The suspension cultures were sub-cultured weekly by transferring 4% of the suspension culture into fresh liquid medium (Example 1).

Suspension cells of a 5 day old suspension culture were either collected for generating the cell packs according the present disclosure or the cells were further cultivated in suspension culture. Both the cell packs and the suspension cultures were incubated for another 4 days. Cell packs of 2 g FCW (fresh cell weight) were prepared as described in example 6 using 14 ml polypropylene columns. Again, constitution of the air voids was carefully monitored and controlled throughout incubation/cultivation by measuring the density of the casted cell pack from which the liquid medium had been removed. Consequently, a relative humidity of 90% was always ensured during the incubation of the cell pack at 26° C. to prevent drying of the cells within the cell pack.

The total soluble proteins from 400 mg FCW samples of the cell packs or of the cells from the suspension culture (separated from the medium by vacuum filtration) were extracted with 2 volumes of extraction buffer (50 mM potassium phosphate, 500 mM NaCl, 10 mM sodium bisulfite, pH 7.5).

Antibodies secreted from the column packed cells were recovered by washing the column packed cells with extraction buffer (Example 6). Briefly, 2 ml buffer was applied to a 2 g column and sucked into the cell pack by a short vacuum. After min incubation the buffer was collected by vacuum and applied again onto the cells. After three consecutive washings 1.6 ml eluate was recovered. Samples collected from the original suspension medium were used for comparison.

Antibody concentrations were measured by SPR on a protein A surface (immobilized by amine-coupling) using purified human antibody H10 produced in CHO cells as standard. All samples were analysed in the linear range of the dose-response curve. DsRed was determined by fluorescence using a DsRed standard.

Despite the fact that the suspension culture had reached a high cell biomass no antibody was detected in the suspension culture supernatant. Thus, the fraction of secreted recombinant product was 0%. The intracellular accumulation of the M12 antibody was 4.02 µg per gram FCW of transgenic BY2 suspension cells. The total yield (antibody in the cell supernatant plus antibody within the cells) was thus also 4.02 µg per gram.

In contrast, the total yield of M12 reached 11.4 µg per gram of cell pack, which corresponds to a substantial total yield increase of 284%. Importantly, it was possible to elute secreted antibody from the cell pack. The yield of secreted product was 1.4 µg M12 antibody per gram of cell pack, which corresponds to 12% of the total yield.

This example demonstrates that it is possible to derive a recombinant protein product from a cell pack generated from a transgenic suspension culture and that yields have been increased significantly by 284% as compared to the control of suspended cells.

The yield of ER-retained DsRed increased 70% in the cells of the cell pack compared to the cells in suspension (5.2 µg/g FCW and 3.0 µg/g FCW, respectively).

This example also clearly illustrates that the incubation of the transgenic suspension cells in the form of a cell pack not only allows the product to be collected in a concentrated manner (compared to the suspension cell culture supernatant) that is highly beneficial for down-stream processing (including a reduction in both process time and costs).

Importantly, the cell pack also provides an excellent entry point for using buffers different from the cell culture medium to maximize the elution of the product (here a recombinant target protein that has been secreted from the cells) and thus the cell pack provides additional benefits over the suspension cells. The supernatants of the suspension culture contained much higher amounts of polysaccharides than eluates from column packed cells. A low amount of polysaccharides is preferred, because the gelatinous polysaccharides hinder down-stream processes like filtration and ultra-filtration.

Furthermore, the percentage of harvested recombinant protein that has been secreted was considerably increased from 0% for the suspension cells to 12% for the cell pack generated according to the invention.

Finally, this example illustrates that the overall yield in the cell pack is also significantly increased compared to the same cells cultivated as suspension cells.

Those skilled in the art will also easily appreciate that this method is not limited to the production and/or isolation of recombinant proteins from transgenic cells but is equally applicable to secondary metabolites produced in non-transgenic or transgenic cells or to other products of interest, including (but not limited to) primary metabolites, fibres, oligo- and polysaccharides (cellulose, starch, hemicelluloses, xylans, fructans, etc.), native peptides and proteins, pigments, vitamins, flavours, fruit acids, or any other products of plant cells.

Example 11

Using Cell Packs Generated in Multi-Titre Plates

Cell packs were generated as explained before using multi-titre plates (Receiver plate 20 µm (No. 740686.4), MACHEREY-NAGEL, Germany) containing liquid permeable filters at the bottom of the plate.

1 ml from a wild-type (non-transgenic) tobacco BY2 suspension culture was casted per well of the receiver plate to generate 96 micro cell packs. The liquid medium was removed completely by vacuum using the NucleoVac 96 Vacuum Manifold from MACHEREY-NAGEL, Germany. The resulting cell packs of 0.2 g were analyzed microscopically for the presence of air voids and the density of the resulting cell pack was confirmed to be less than 0.7 g/cm$^3$ using an independent control experiment.

0.8 ml of recombinant *Agrobacterium tumefaciens* suspension (OD600 nm=0.1) carrying pTRA plasmids encoding for either the antibody M12 (FIG. 2C) or for the antibody 2G12 (FIG. 2A) were applied to each cell pack. For each antibody expression construct 32 micro cell packs were infiltrated. After 30 minutes any liquid was removed to reconstitute the air voids and to re-establish a cell pack density of less than 0.7 g/cm$^3$. The cell packs in the multi-titre plate were then incubated for 4 days at 25° C. and 90% relative humidity. Then, the cell packs were harvested and the recombinant antibodies were extracted (Example 1). The antibody concentrations were measured by surface plasmon resonance measurements on a protein-A surface using a BiacoreT200 instrument (T=25° C., Running Buffer=HBS-EP) for 32 samples for each antibody to determine the mean antibody concentration and the coefficient of variation (CV).

The mean yield of the antibody M12 was 117.8±14.4 µg per g cell pack and the coefficient of variation was 12.2%. The mean yield of the antibody 2G12 was 32.3±3.6 µg per g cell pack and the coefficient of variation was 11.1%.

These are excellent values for biological assays and clearly illustrate the excellent reproducibility and robustness of assays based on the cell packs prepared according to the invention.

This also shows that different sizes and geometries of the cell pack can be used for different applications and this experiment demonstrates that cell packs can be generated in multi-titre format, which facilitates high-throughput applications at high resolution.

Furthermore, it is also clear that the cell packs in multi-titre format can be handled and treated in the same or similar way as those casted in columns, including elution of secreted or extracellular products, for subsequent quantification or analysis.

Those skilled in the art will acknowledge that the cell packs can also be used for analytical purposes. For example, a cell pack generated from a transgenic suspension culture or a cell pack transformed with genes for recombinant antibodies, including (but not limited to) for example antibody-fusion proteins to the cellulose binding protein or recombinant antibodies attached to or integrated into the cell membrane (plasmalemma) can be brought into contact with a solution (sample) containing a substance that binds to the antibody. The porous nature of the cell pack is again a clear advantage here because large volumes can easily be passed through the cell pack to increase the sensitivity. Moreover, it is obvious that washing steps, buffer exchanges and application of enzyme conjugated antibodies or other detection reagents can also easily be applied and removed from the cell pack. In a final step a substrate can be applied that is then transformed enzymatically into a measurable product to reveal the presence and concentration of the substance.

Example 12

Endogenous Protein Recovered from a Cell Pack Generated from Wild Type Cells

Figure 16:
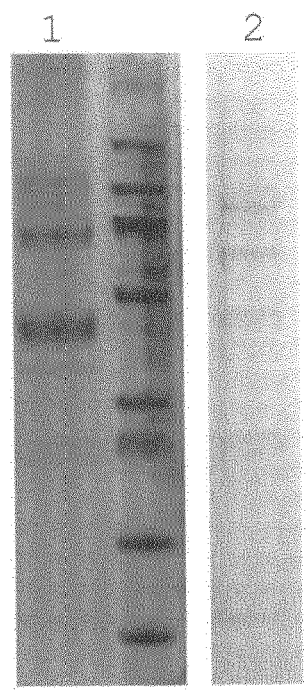
FIG. 16 shows a Coomassie-stained SDS-PAGE gel of an eluate of 4 day old column packed cells generated from a 5 day old BY-2 wild type suspension culture (1) and of the culture medium of the corresponding 9 day old BY-2 wild type suspension culture (2).

Suspension cells of a 5 day old BY-2 wild type suspension culture were either collected for generating the cell packs or the cells were further cultivated in suspension culture. Both the cell packs and the suspension cultures were incubated for another 4 days. A cell pack of 2.5 g FCW (fresh cell weight) was prepared as described in example 6 using 14 ml polypropylene columns. After removal of the liquid, the cell pack was incubated at 26° C. with a relative humidity of 90%. The 5 day old BY-2 suspension culture was further cultivated at 26° C. on a rotary shake at 180 rpm. After 4 days secreted proteins were harvested. The secreted proteins were harvested from the cell pack by washing the pack with 2.5 ml buffer as described in example 6. The secreted proteins from the 9 day old suspension culture were harvested by removing the cells from the culture medium using vacuum filtration. A 25 µl sample of either the eluted or the secreted proteins were analyzed on a Coomassie-stained SDS-PAGE gel (FIG. 16). This example shows that secreted native proteins can be recovered from cell packs generated and incubated according to the invention. Each band on the gel represents a different natural protein. The gel analysis also showed that amount and sort of the secreted native proteins differed between cells in a cell pack and cells in suspension. The secretion of certain native proteins are substantially increased in the cells of a cell pack (FIG. 16, indicated by arrows).

Those skilled in the art will also easily appreciate that this method is not limited to the recovery of native proteins from plant cells but is equally applicable to other endogenous products of interest, including secondary metabolites, primary metabolites, fibres, oligo- and polysaccharides (cellulose, starch, hemicelluloses, xylans, fructans, etc.), native peptides and proteins, pigments, vitamins, flavours, fruit acids, or any other product of plant cells. Those skilled in the art will recognize that cell packs can be generated from suspension cells selected from a broad variety of plant species, including but not limited to *Catharanthus roseus*, *Taxus* spec., *Stevia rebaudiana* and *Artemisia annua*.

The invention claimed is:

1. A method for the generation and maintenance of plant cell material in the form of a medium-deprived, porous structured and non-tissue multilayer cell pack, the method comprising the steps of:
    (i) forming a cell pack of cells by separating said cells from a plant cell suspension culture, wherein the cells are native or transgenic and able to accumulate a desired product, and adjusting the liquid content of the cell pack to a cell pack density between 0.1 and 0.9 g wet cell weight per cm$^3$ to form air voids between cells within the cell pack, thereby establishing a porous structured and non-tissue multilayer cell pack that is medium deprived; and
    (ii) incubating the medium-deprived, porous cell pack under a relative humidity of 50 to 100% in order to accumulate the desired product while maintaining air voids in the cell pack, wherein incubation is carried out without placing the medium-deprived and porous structured cell pack on or in any contact with a maintenance or growth medium.

2. The method according to claim 1, wherein the liquid content is adjusted to correspond to a cell pack density between 0.2 and 0.85 g wet cell weight per cm$^3$, optionally between 0.4 and 0.8 g wet cell weight per cm$^3$.

3. The method according to claim 1, wherein the cells are either transiently or stably transformed in order to accumulate the desired product.

4. The method according to claim 1, wherein the separated cells are transiently transformed with at least one expression vector comprising at least one heterologous nucleic acid sequence before encoding the desired product before the step of incubating the medium-deprived porous cell pack.

5. The method according to claim 1, further comprising harvesting the desired product.

6. The method according to claim 1, wherein the desired product is selected from the group consisting of native and heterologous proteins or polypeptides, secondary metabolites, and markers.

7. A method of using plant cell material for analytical or diagnostic purposes, the method comprising performing the method of claim 1, wherein the step of incubating the medium-deprived porous cell pack is performed in the presence of an organism or of a substance to be analyzed or diagnosed.

8. The method according to claim 1, wherein the method further comprises temporarily flooding the voids with a liquid then removing the liquid to reconstitute the air void between the cells.

9. The method according to claim 8, wherein the flooding elutes the desired product from the cell pack.

10. The method according to claim 1, wherein the incubation step is performed for at least one day.

11. The method according to claim 1, wherein the incubation step is performed for 2-7 days.

12. The method according to claim 1, wherein the cell pack is provided in a column and the incubation is conducted in the column.

13. The method according to claim 12, further comprising eluting the desired product from the column by flooding the voids with a fluid and collecting the eluate.

14. The method of claim 1, wherein the cell pack is a non-tissue, multilayer conglomerate of cells.

15. A method for the generation and maintenance of a cell pack, the method comprising:
(i) forming a cell pack comprising a conglomerate of cells at a cell pack density between 0.1 and 0.9 g wet cell weight per $cm^3$, wherein the cell pack comprises air voids between cells of the cell pack, further wherein the cell pack is not tissue, further wherein cells within the cell pack are able to express a desired product;
(ii) incubating the cell pack to express the desired product, wherein the incubation is at 50-100% humidity and maintains air voids between the cells;
(iii) flooding the air voids with a liquid media to elute the desired product;
(iv) collecting the eluted product; and
(v) reconstituting the cell pack with air voids.

16. The method of claim 15, wherein the cells that express the desired product are transgenic cells.

17. The method of claim 15, wherein the desired product is a polypeptide.

18. The method of claim 15, wherein the desired product is an antibody or an antibody-fusion protein.

19. The method of claim 15, wherein the steps of incubating and flooding are performed in a column.

20. The method according to claim 1, wherein the liquid content is adjusted to correspond to a cell pack density between 0.54 and 0.85 g wet cell weight per $cm^3$.

* * * * *